US006460399B1

(12) United States Patent
Beekman et al.

(10) Patent No.: US 6,460,399 B1
(45) Date of Patent: Oct. 8, 2002

(54) COMPRESSION TEST METHOD AND APPARATUS FOR DETERMINING GRANULE STRENGTH

(75) Inventors: Willem Johan Beekman; Gabriel M. H. Meesters, both of Delft; Brian Scarlett, Den Haag, all of (NL)

(73) Assignee: Genencor International, Inc., Palo Alto, CA (US)

( * ) Notice: Subject to any disclaimer, the term of this patent is extended or adjusted under 35 U.S.C. 154(b) by 73 days.

(21) Appl. No.: 09/712,034

(22) Filed: Nov. 14, 2000

(51) Int. Cl.$^7$ ............................................... G01M 7/00
(52) U.S. Cl. ........................................ 73/12.09; 73/821
(58) Field of Search ............................ 73/12.01, 12.04, 73/12.06, 12.09, 12.11, 12.12, 12.13, 818, 819, 821–824

(56) References Cited

U.S. PATENT DOCUMENTS

| | | | | |
|---|---|---|---|---|
| 3,653,256 A | * | 4/1972 | Mashimo | 73/81 |
| 4,160,325 A | | 7/1979 | DeNicola | 33/148 |
| 5,154,086 A | * | 10/1992 | Porchia et al. | 73/818 |
| 5,753,822 A | * | 5/1998 | Hock | 73/805 |
| 5,808,201 A | * | 9/1998 | Hugentobler | 73/597 |
| 5,967,434 A | * | 10/1999 | Virk | 241/169.1 |
| 6,035,716 A | | 3/2000 | Beekman et al. | 73/579 |
| 6,173,601 B1 | | 1/2001 | Beekman et al. | 73/7 |
| 6,357,282 B1 | * | 3/2002 | Benjamin | 73/81 |

OTHER PUBLICATIONS

Reetz, "Granulatfestigkeits–Prüfung" *Materialprüfung* 33 (1991) 7–8, pp. 219–222, with partial translation.

Schulle, "Beurteilung der Festigkeit von Einzelgranalien und Auswirkungen auf das Pressverhalten von Granulaten" *Keramische Zeitschrift*, 47, Jahrgang Nr. 7, (1995), pp. 534–535, with partial translation.

Darvell, "Uniaxial compression tests and the validity of indirect tensile strength" *Journal of Materials Science* 25 (1990) pp. 757–780.

Yashima et al. "Mechanical Properties of Brittle Materials and Their Single Fracture under Dynamic Loading" Science Report of the Research Institute, Toholen University 31(2), (1983), pp. 254–269.

Beekman et al., "Measurement of Granule Impact Strength Distributions by Using a Vibrating Container Filled with Granules." *World Congress of Chemical Engineering*, San Diego, California, Jul. 14–18, 1996.

* cited by examiner

*Primary Examiner*—Max Noori
(74) *Attorney, Agent, or Firm*—Kilyk & Bowersox, P.L.L.C.

(57) ABSTRACT

A method and apparatus for the accurate monitoring of a granule during compression testing is provided and enables the study of breakage mechanisms that cause particle failure during compression. The method involves compressing a granule or particle with the apparatus and the apparatus is a spring device that combines a spring in parallel with the granule or particle and a spring in series with the granule or particle. Under failure conditions, sudden deformation of the granule or particle results in fast relaxation of the granule or particle during breakage and allows very careful granule breakage. Measuring or recording devices coupled to the apparatus provide for the detailed study of breakage conditions at the moment of failure and lend incite into the compression strength characteristics of the granule or particle.

36 Claims, 9 Drawing Sheets

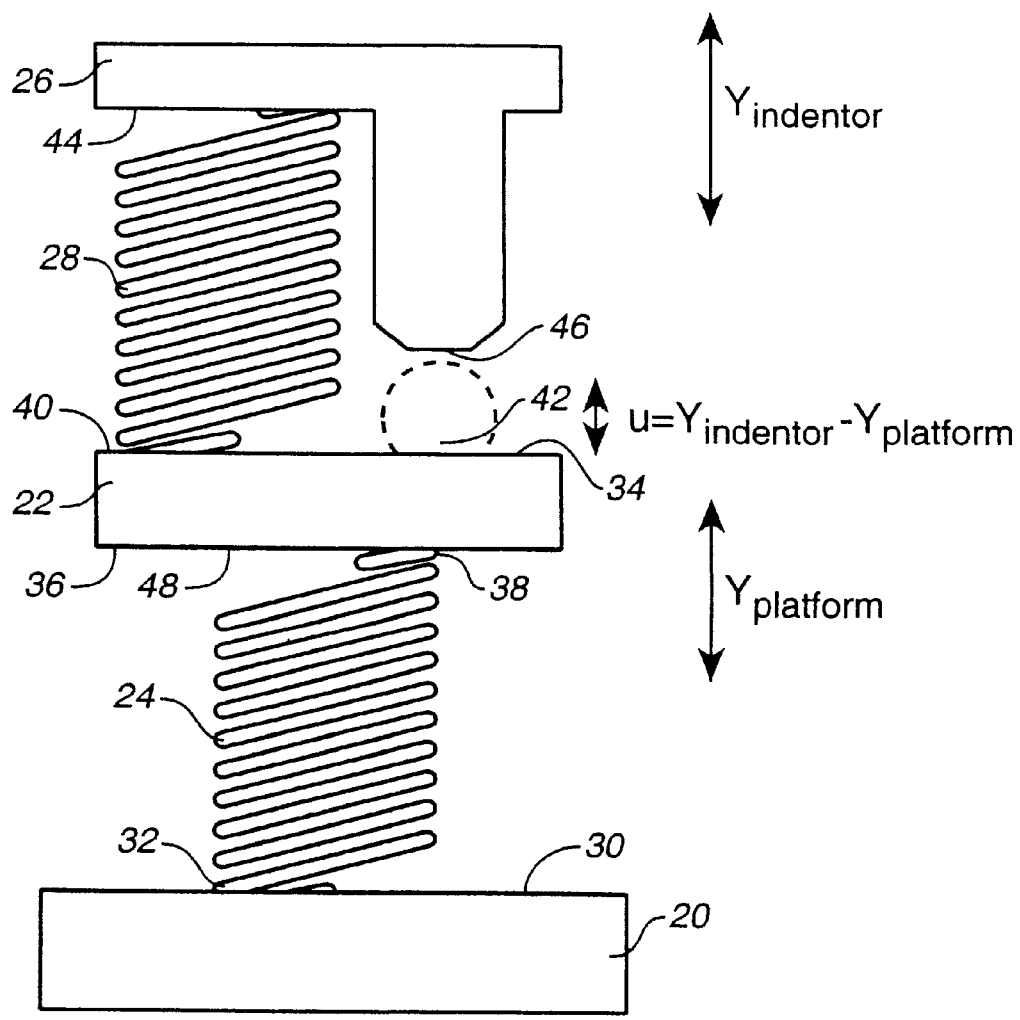
FIG._1

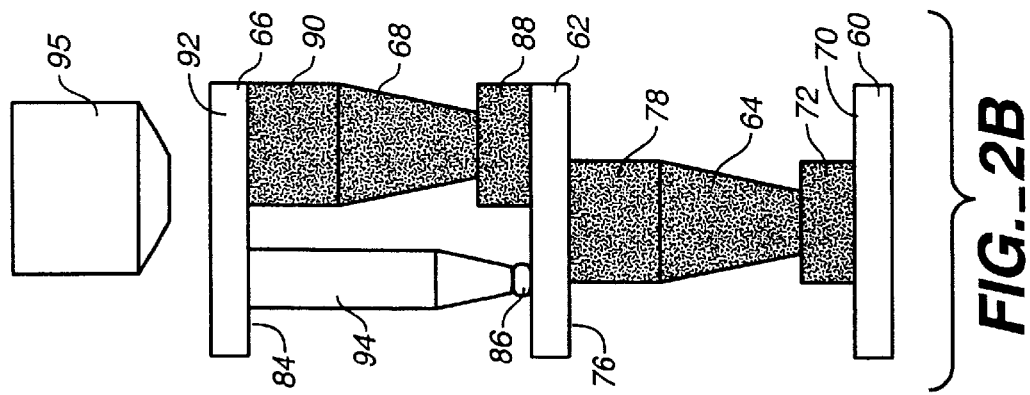
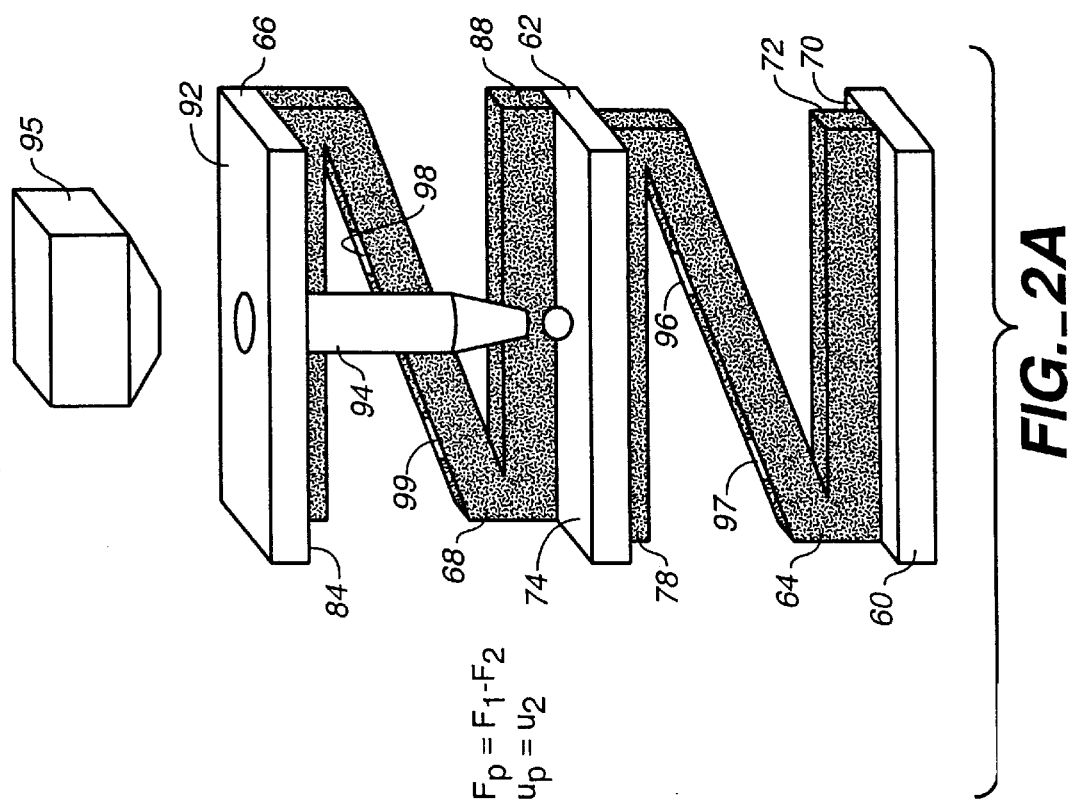
$F_p = F_1 - F_2$
$u_p = u_2$

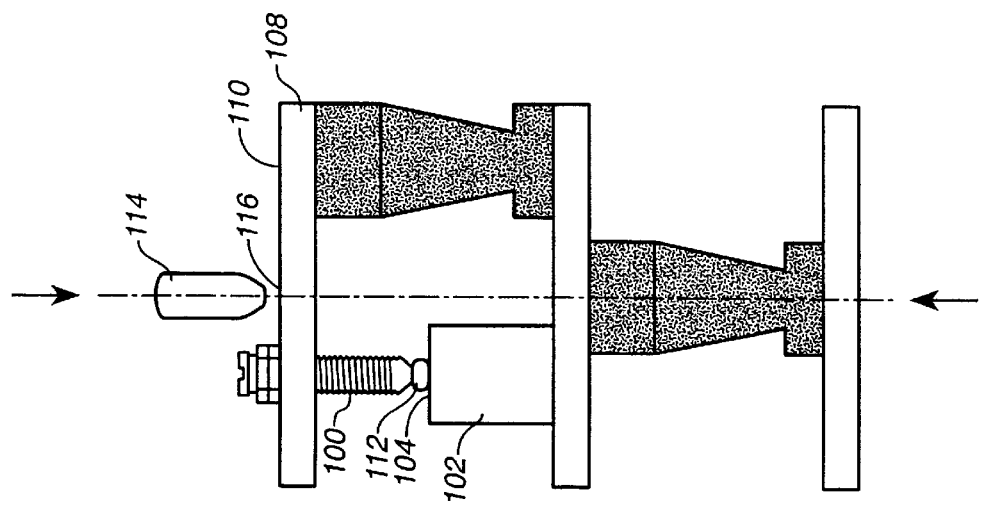
FIG._3B
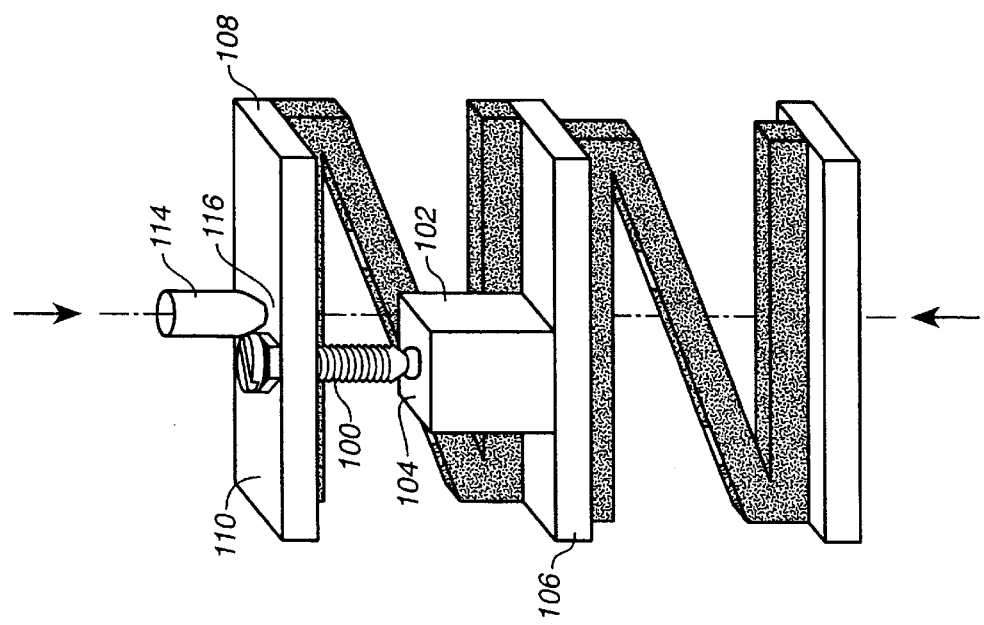
FIG._3A

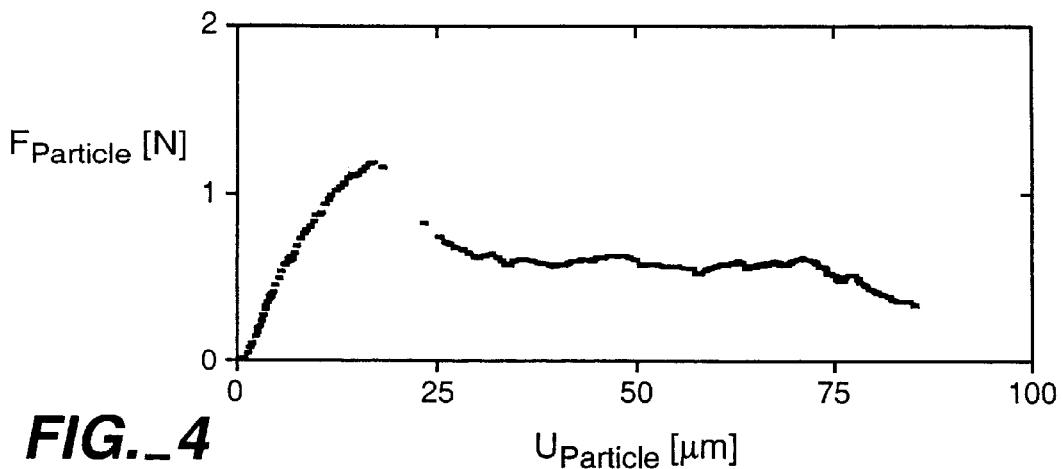
FIG._4
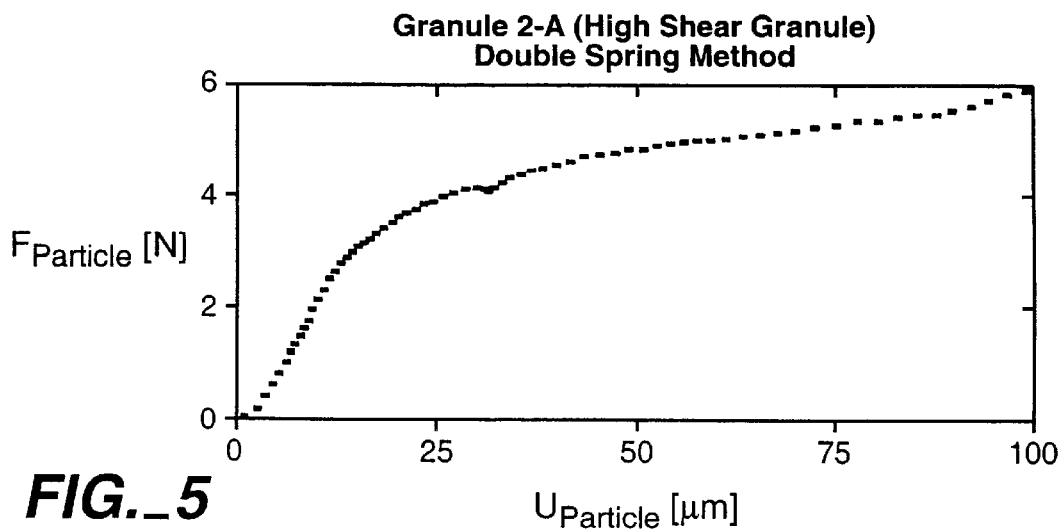
FIG._5
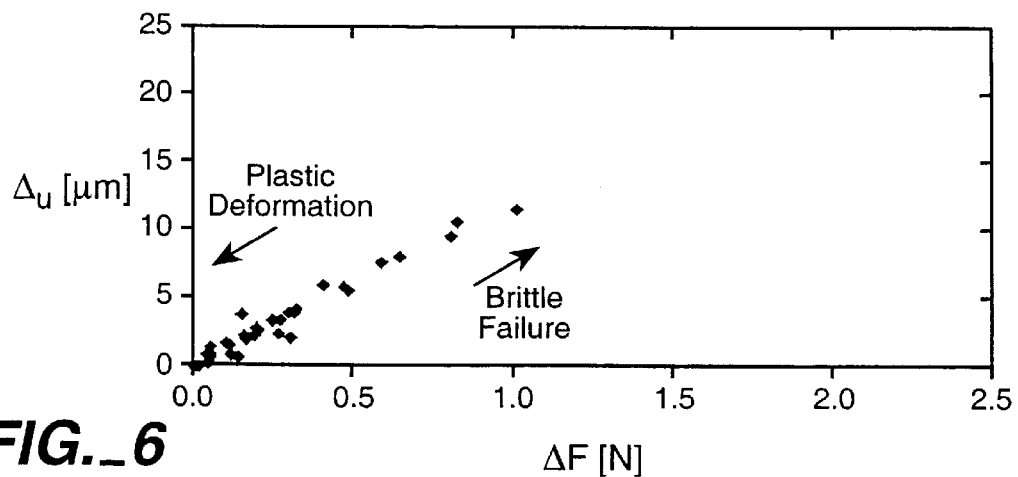
FIG._6

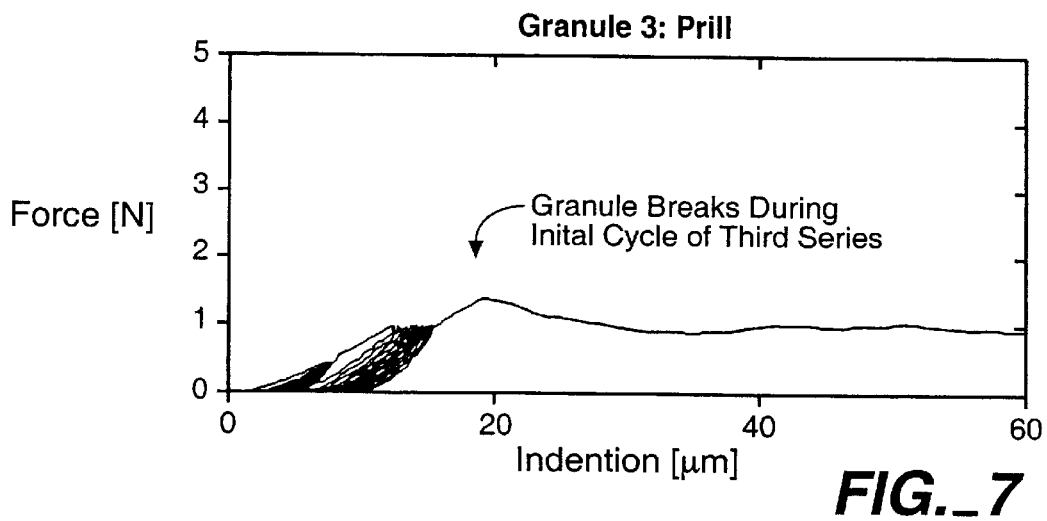
FIG._7
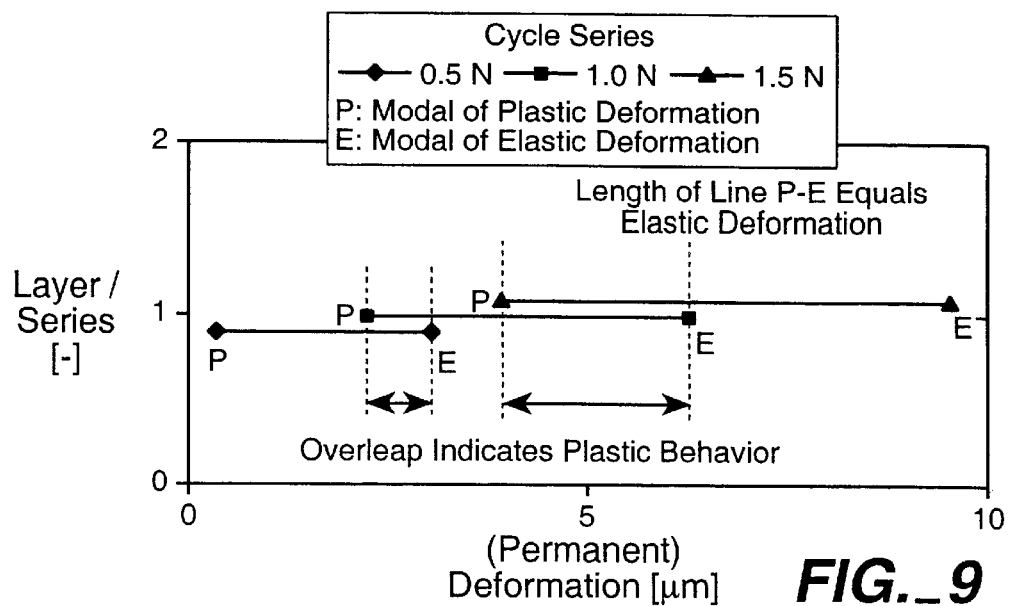
FIG._9

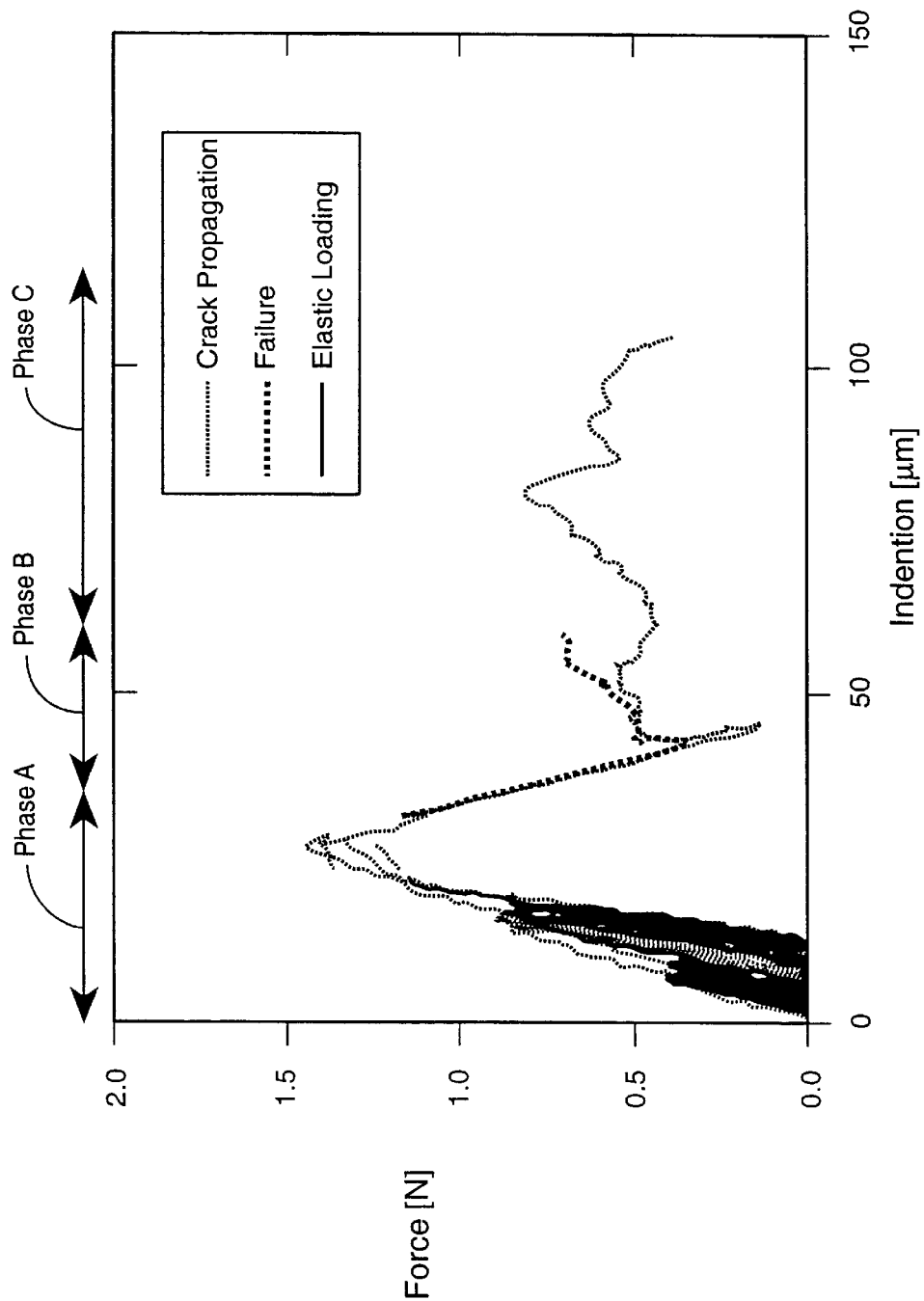
FIG._8

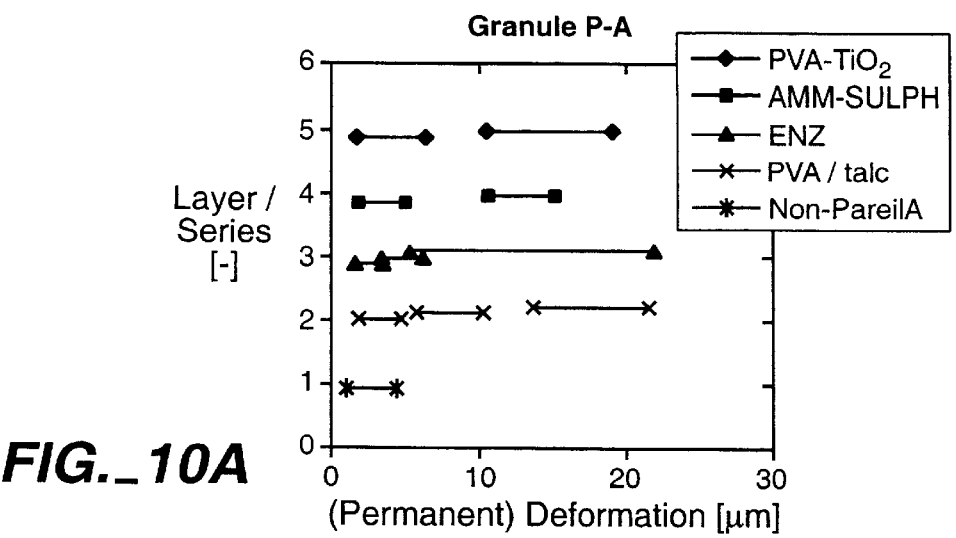
FIG._10A
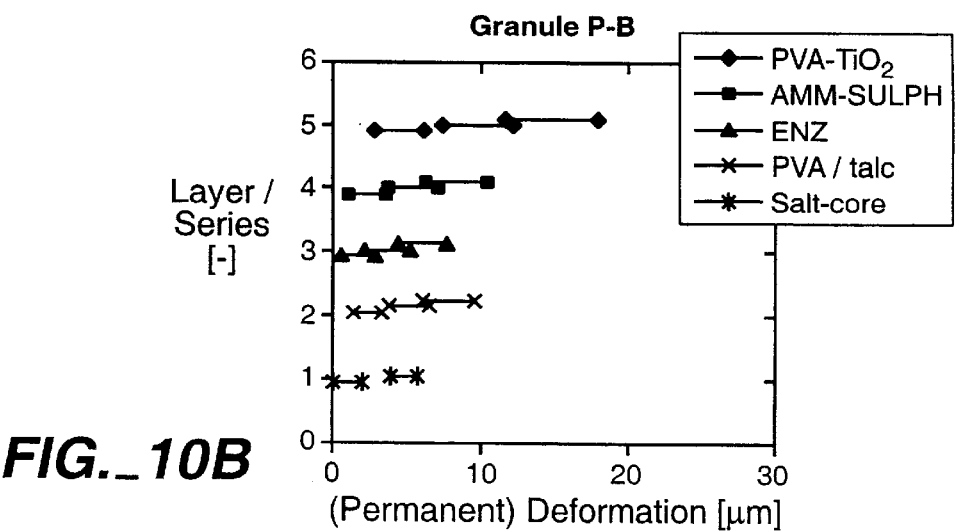
FIG._10B
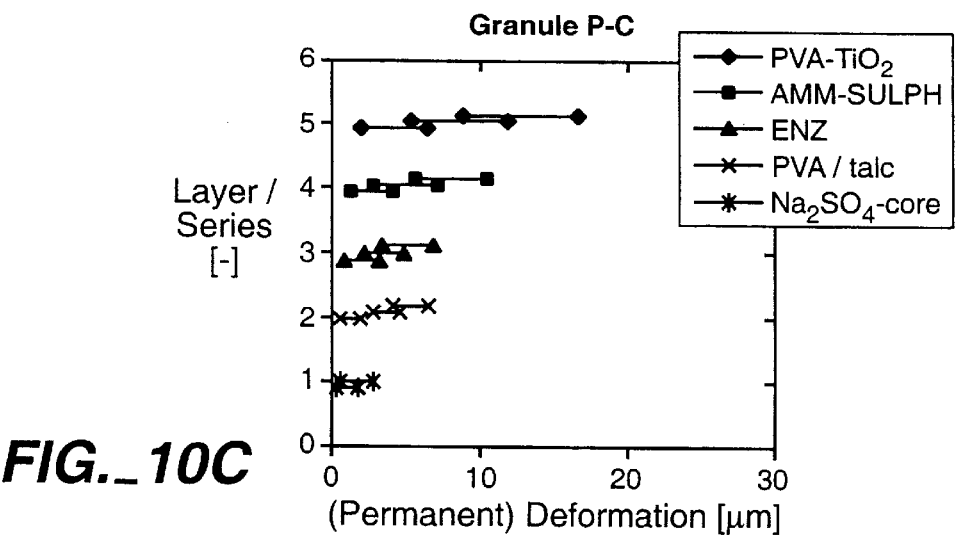
FIG._10C

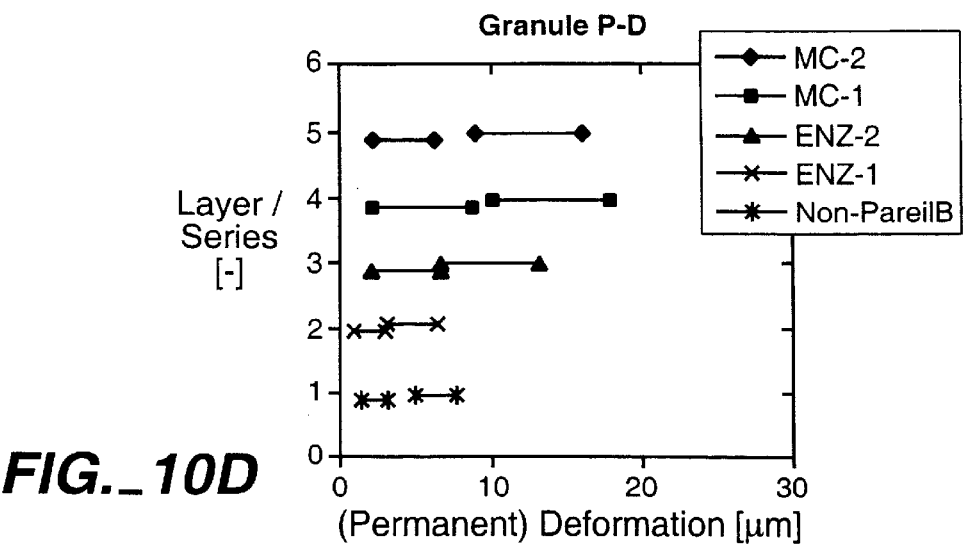
FIG._10D
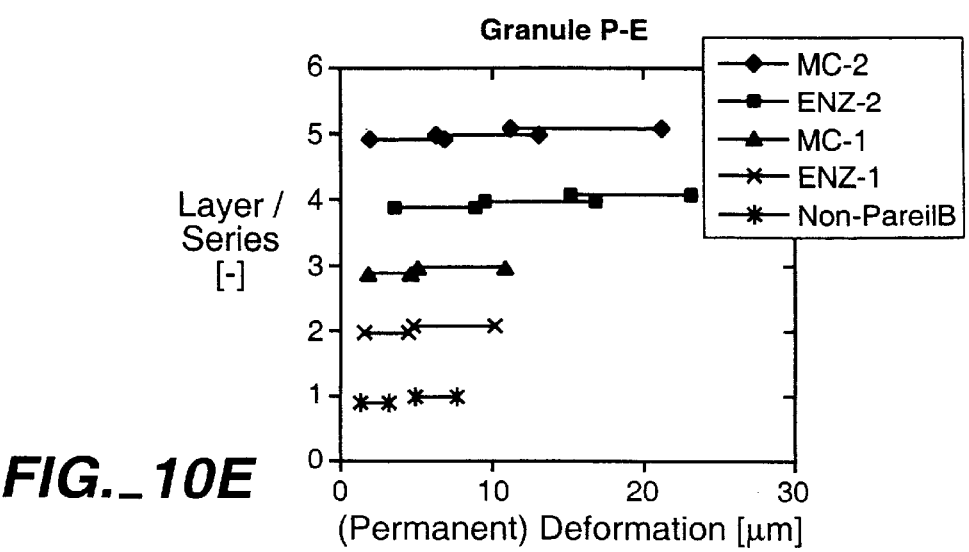
FIG._10E
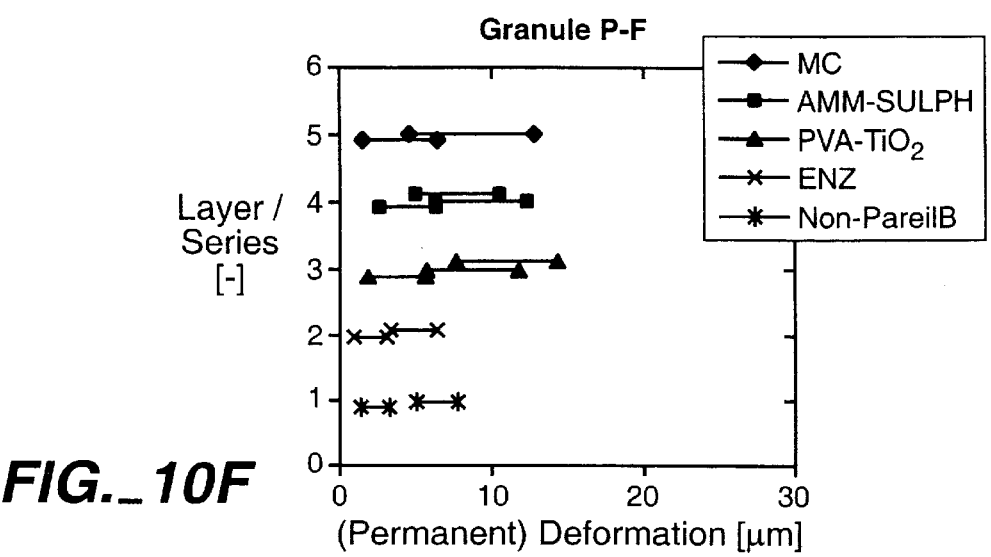
FIG._10F

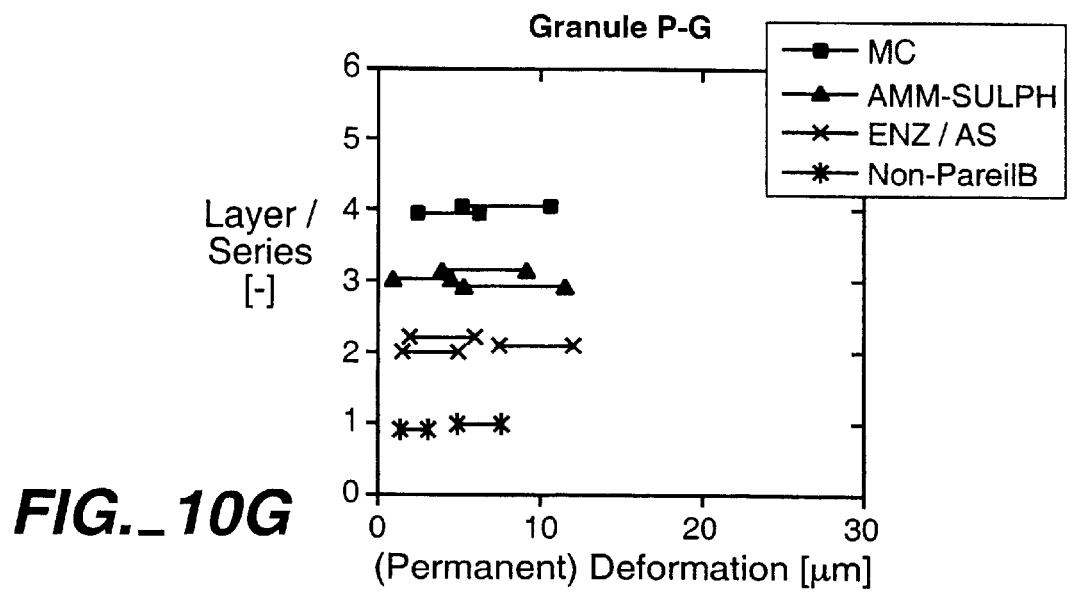
FIG._10G
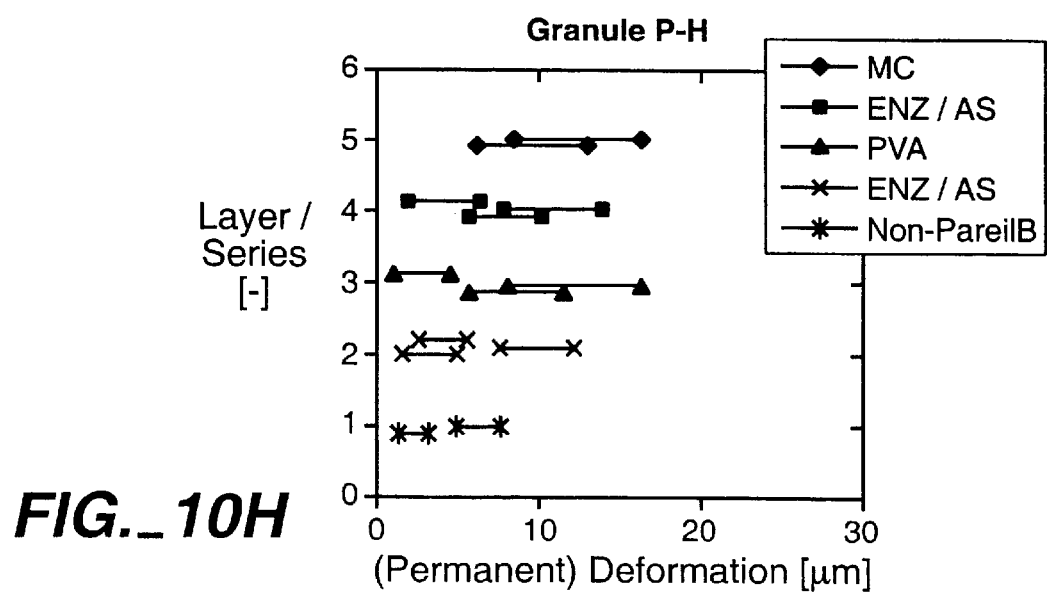
FIG._10H

COMPRESSION TEST METHOD AND APPARATUS FOR DETERMINING GRANULE STRENGTH

FIELD OF THE INVENTION

The present invention relates to a method and apparatus for testing the compression strength of a granule. More particularly, the present invention relates to a method and apparatus for determining the breakage mechanism involved with the compressive failure of a granule.

BACKGROUND OF THE INVENTION

Many food products, detergents, pharmaceuticals and industrial intermediates are available as granular materials. Industry produces these granules by agglomeration processes from fine powders or slurries. Granulation conditions that are needed to obtain granules with acceptable mechanical properties are often set by trial and error, as a fundamental understanding of agglomeration processes and granule strength measurements has, before now, been limited. A number of particle strength tests are reported in literature, which often are only share in common the ability to generate and quantify particle breakage. Tests intended to assess granule breakage show a large spread in measured results or show very complicated particle-particle interaction. In both cases, interpretation of particle breakage results is difficult.

Particle breakage can be distinguished in attrition, fracture, abrasion and chipping. Small-scale damage due to normal forces is called attrition; large-scale catastrophic damage is called fracture. Small-scale incidental damage due to tangential forces results in polishing of the granule and is called abrasion. If impacts cause substantial tangential force on the granule and result in local damage to the particle surface, the breakage is called chipping.

U.S. Pat. No. 6,035,716 describes a repeated impact test method and apparatus that measures damage to granules under high velocity forces. This and other impact tests, however, do not predict damage to granules under static compression or low velocity forces. A need exists for a test method and apparatus to study damage and breakage of granules and particles under low velocity forces or static compression conditions.

Particle compression tests have been performed to obtain an insight in the mechanical quality of granules. In these tests, two parallel plates squeeze a granule after which the force and deformation of the particle is registered. Though the experiments are easy to conduct, interpretation of the obtained curves is in most cases complicated. Failure as a result of compression is a complicated phenomenon.

Compression experiments have been reported either with a constant deformation rate or with a constant loading rate. In a first method, two parallel plates compress a granule at a constant deformation rate. In a second method, two parallel plates compress granules with constant force increments. In the first method, compression with a constant deformation rate or compression with a constant indention velocity has to take place at an extremely low indention velocity. This in done in an attempt to monitor the breakage process, notwithstanding the fact that the measurements become very time consuming. A lot of attention has been paid in literature to the effect of compression speed on particle breakage force. Efforts have been made to deduce a material strength parameter from compression experiments (e.g. Yashima, 1979, Schulle, 1995). Regardless of such efforts, a method and apparatus for accurately monitoring the breakage process under compressive failure of a particle has still not been achieved, let alone for accurately monitoring the process.

The Zwick Texture Analyzer is a compression set-up based on this principle, as are compression test apparatus available from Instron. The Zwick device is equipped with with an accurate load cell to assess breakage strength of granules. It has a maximum load range of 50 Newtons and a resolution of 0.001 Newton. The device includes a blunt indentor that is moved by screw action from above a particle toward the particle on an anvil. The spatial resolution of the device is about 20 micrometers. Results with such a device show that only limited information about the breakage of the particle can be obtained. The spatial resolution information provided from such a device is insufficient for adequately studying breakage behavior. It was impossible to determine the difference between elastic and plastic loading. Furthermore, elastic energy is stored in the system.

In another method, compression with a constant loading rate or constant force increments does not allow monitoring of the breakage process itself for partly brittle particles. When the particle starts failing, the indentor moves further towards the granule while trying to increase the load on the particle. This leads to more damage to the granule, which then falls apart into fragments. Therefore no information is obtained about the breakage process of the particles.

In these and similar devices, elastic energy becomes stored in the system when a granule is tested and when the granule suddenly breaks, part of the stored energy is released and the indentor is accelerated toward the granule. Because the granule has no effective means of draining this energy, it is likely to collapse.

The use of a compression apparatus including a piezoelectric device has been tried with a constant indentation speed mode and provides good spatial resolution. However, at the point of breakage no results are obtained because the granule tested is smashed.

All references mentioned herein are incorporated herein in their entireties by reference.

A need exists for an apparatus and method for accurately and more quickly monitoring the breakage process of a particle under compression testing conditions and for determining the breakage mechanism of the particle.

A need further exists for an apparatus and method for accurately and more quickly monitoring repeated compression testing on a particle and for determining the breakage mechanism of the particle.

SUMMARY OF THE PRESENT INVENTION

The present invention provides a method and apparatus for the accurate monitoring of a granule during compression testing and for the determination of the breakage mechanism that causes particle failure. Although the invention will be described in connection with the testing of granules, particles, or both, it is to be understood that the invention is applicable for the testing of other objects as well, such as particles, agglomerates, molded objects, and the like.

According to the present invention, a granule is compressed with a double spring compression device that enables the study of the process of granule breakage in more detail. This is achieved by a combination of a spring in parallel and a spring in series with the granule. With the apparatus of the present invention, sudden deformation of the granule results in fast relaxation of the granule during breakage and allows very careful granule breakage.

The apparatus according to an embodiment of the present invention includes a bottom plate, a platform, an indentor, top and bottom biasing members, and a measuring or recording device. The bottom plate has a top surface and a bottom surface. The platform has a top surface and an opposite bottom surface and the bottom surface faces the bottom plate. The platform top surface includes a biasing portion, and a contact portion for contacting a granule to be tested. The bottom biasing member is positioned between the bottom plate and the platform and is preferably in contact with both the top surface of the bottom plate and the bottom surface of the platform. The bottom biasing member biases or forces the platform away from the bottom plate. The indentor has an indentor bottom surface facing the platform and a contact surface extending below the indentor bottom surface in a direction toward the platform. The indentor contact surface faces the platform and contacts a granule to be tested that is positioned on the platform. The top biasing member is positioned between the top surface of the platform and the indentor bottom surface and is in contact with both the indentor bottom surface and the biasing portion of the platform top surface. The top biasing member biases or forces the indentor away from the platform. The measuring or recording device measures the force exerted on a granule to be tested under force exertion conditions.

The method of the present invention involves using an apparatus of the present invention to study the compression characteristics and breakage mechanisms of a granule or particle. The method includes: providing a compression testing apparatus as described above; positioning a granule to be tested on the platform in contact with the contact portion of the platform and between the contact portion of the platform and the contact surface of the indentor; exerting a force on the indentor in a direction toward the platform sufficient to move the contact surface of the indentor into contact with the granule and to exert a compressive force on the granule; and measuring the compressive force exerted on the granule. The method can further involve recording the measured forces and determining a breakage mechanism by analyzing the measured forces.

It is to be understood that both the foregoing general description and the following detailed description are exemplary and explanatory only and are intended to provide further explanation of the present invention, as claimed.

BRIEF DESCRIPTION OF THE DRAWINGS

The invention may be more fully understood with reference to the accompanying figures. The figures are intended to illustrate exemplary embodiments of the present invention without limiting the scope of the invention.

FIG. 1 is a schematic diagram of a double spring compression test apparatus according to an embodiment of the present invention;

FIGS. 2A–2B are schematic diagrams of a double spring compression test apparatus according to another embodiment of the present invention;

FIGS. 3A–3B are schematic diagrams of a double spring compression test apparatus according to yet another embodiment of the present invention;

FIG. 4 is a schematic drawing of a force displacement curve identifying three different stages of compression behavior—elastic loading, particle failure, and further crack opening;

FIG. 5 is a force displacement curve for high shear granule particle;

FIG. 6 is a graph showing the relationship between an observed drop in force ($\Delta F$) and the step in deformation upon breakage ($\Delta u$) caused by a compression test method;

FIG. 7 is graph showing the stress-strain curves obtained by repeated compression test measurements conducted on a spherical enzyme-containing prill granule;

FIG. 8 is a graph showing the three phases of a force displacement diagram of a repeated compression experiment conducted in accordance with a method of the present invention that makes plastic deformation visible;

FIG. 9 is a graph showing the median of the range of plastic and elastic deformations observed and the median of total deformations observed as a result of testing a layered granule in accordance with a method of the present invention; and FIGS. 10A–10H are graphs showing the median of the range of plastic and elastic deformations observed and the median of total deformations observed as a result of testing various layered granules in accordance with a method of the present invention.

DETAILED DESCRIPTION OF THE PRESENT INVENTION

The apparatus according to an embodiment of the present invention includes a bottom plate, a platform, an indentor, top and bottom biasing means, and a measuring or recording means such as a measuring or recording device. The bottom plate has a top surface and a bottom surface. The platform has a top surface and an opposite bottom surface and the bottom surface faces the bottom plate. The platform top surface includes a biasing portion, and a contact portion for contacting a granule to be tested.

The bottom biasing means is preferably a biasing member, for example, a Z-spring, a coil spring, a leaf spring, another type of spring, an elastic member, a hydraulically-operated piston, a gel, a gas cylinder, and the like. The biasing member is preferably positioned between the bottom plate and the platform and is preferably in contact with both the top surface of the bottom plate and the bottom surface of the platform. The bottom biasing member biases or forces the platform away from the bottom plate.

The top biasing means is also preferably a biasing member, for example, a Z-spring, a coil spring, a leaf spring, another spring type, an elastic member, a hydraulically-operated piston, a gel, a gas cylinder, and the like. The top biasing member is preferably positioned between the top surface of the platform and the indentor bottom surface and is preferably in contact with both the indentor bottom surface and the biasing portion of the platform top surface. The top biasing member biases or forces the indentor away from the platform.

Preferably, the bottom and top biasing members have substantially the same force constants. Preferably, both the bottom biasing member and said top biasing member are springs and more preferably, the bottom biasing member and the top biasing member have substantially the same spring constant. According to a preferred embodiment, the bottom biasing member and the top biasing member are both Z-springs.

For measuring the force exerted on a granule or particle being tested, at least the top biasing member is preferably provided with at least one means for measuring force or strain, such as a strain gauge. The strain gauge preferably is arranged to measure the strain or force exerted parallel to a granule positioned between the contact surface of the indentor and the contact portion of the platform. Preferably, both the bottom and top biasing members are provided with at least one respective strain gauge.

According to a preferred embodiment of the present invention, the bottom biasing member and the top biasing member have respective force constants, and the force constants of the biasing members are selected or provided to provide for a reduction in the compressive force exerted on a granule compressed between the contact portion of the platform and the contact surface of the indentor, upon breakage of the granule.

According to a preferred embodiment of the present invention, the top biasing member and the bottom biasing member each comprise a Z-spring having top and bottom horizontal legs. Preferably, the horizontal legs remain substantially parallel to each other during compression of the Z-springs.

The indentor has an indentor bottom surface facing the platform and a contact surface extending below the indentor bottom surface in a direction toward the platform. The indentor contact surface faces the platform and contacts a granule to be tested that is positioned on the platform.

According to embodiments of the present invention, the indentor is not a single unitary piece but rather includes a top plate that provides the indentor bottom surface, and a second, but connected, portion that is a contact member which extending from the indentor toward the platform. According to such an embodiment, the contact member has an upper end in contact with the top plate and a lower end that includes the contact surface.

The apparatus of the present invention preferably also includes a means for exerting a force on a granule to be tested, for example, a force exertion device for exerting a force on the indentor to move the indentor in a direction toward the platform. The force exertion device may be a hydraulically-operated or screw-operated press, a piston, a lever-operated counterplate, or the like. The force exertion device preferably is capable of providing a force sufficient to compress a granule or particle being tested to the point of breakage. Preferably, the force exertion device provides sufficient force to provide a pressure of from about 1 to about 30,000 pounds per square inch (psi), more preferably from about 1 to about 7500 psi from the contact surface of the indentor on a granule or particle being compressed.

The measuring or recording means or device measures the force exerted on a granule to be tested under force exertion conditions. Preferably, the measuring means or device includes a recording device that records the force exerted on a granule being tested, records the deformation of the granule, and compares or plots the recorded exerted force versus the deformation of the granule. Accordingly, the measuring means or device may include a plotting or graphing device. An exemplary measuring means or device could include a force gauge or a strain gauge coupled to an analog-to-digital interface and a computer.

Preferably, the testing apparatus of the present invention exhibits a mass spring system resonance frequency (f) whereby the top biasing member has a force constant $C_1$, the bottom biasing member has a force constant $C_2$, the platform has an effective mass ($m_{eff}$), and the mass spring system resonance frequency (f) has a cycle time ($\tau=1/f$) according to the formula:

$$\tau=\sqrt{m_{eff}/(C_1+C_2)}$$

The method of the present invention involves using an apparatus of the present invention to study the compression characteristics and breakage mechanisms of a granule or particle. The method includes: providing a compression testing apparatus as described above; positioning a granule to be tested on the platform in contact with the contact portion of the platform and between the contact portion of the platform and the contact surface of the indentor; exerting a force on the indentor in a direction toward the platform sufficient to move the contact surface of the indentor into contact with the granule and to exert a compressive force on the granule; and measuring the compressive force exerted on the granule. The method can further involve recording the measured forces and determining a breakage mechanism by analyzing the measured forces.

The method of the present invention can further include the step of continuing to exert a compressive force on a granule at least until the granule breaks. Preferably, the method includes recording the compressive force exerted on the granule versus the deformation of the granule during compression. One method of determining the force exerted on the granule involves measuring the compressive force parallel to the granule, and calculating the force exerted on the granule by determining the difference between the recorded force exerted on the indentor and the recorded force parallel to the granule. These various forces can be measured with strain gauges, for example, and can be measured by strain gauges positioned in the biasing means, for example, in a Z-spring biasing means.

By analyzing the relationship between the recorded force exerted on the granule and the recorded deformation of the granule during compression, a granule breakage mechanism can be assessed based on the analysis. Given known curves of granules with known breakage mechanisms, comparisons can be made to extrapolate the breakage mechanism of any given granule tested. For example, comparisons can be made between results recorded from testing a granule with recorded results obtained from substantially identical testing performed on granules with known breakage mechanisms.

In principle, the force displacement curves of a semi-static compression experiment show three different stages. The first stage is called elastic loading and is characterized by the fact that when a force on a granule increases, the area of contact between the particle and upper and lower counterplates increases as well. The deformation of the particle is nearly elastic and reversible. The second stage is called particle failure or breakage. This is an often easily recognizable stage wherein the particle starts deviating from ideal (and smooth) behavior. Often, during this stage, the particle develops a simple geometry of cracks. More complicated ways of failure can happen as well. Plastic yielding can result in a slow particle failure process and in strong deviations from the ideal brittle elastic behavior. The third stage is referred to as further crack opening and propagation or further debris compression. During this phase the counterplates start to break debris from the granules. This makes the results very difficult to analyze but often comprises the most important stage in determining the breakage mechanism of the particle. These three phases can be recognized in the schematic drawing of a force displacement curve shown in FIG. 4 and are discussed in more detail in the Examples set forth below.

According to another embodiment of the present invention, repeated compression testing can also be performed using the apparatus of the present invention. Repeated compression testing preferably involves reducing the force exerted on the granule and repeating the exertion of force on the granule. By recording the compressive force exerted on the granule versus the deformation of said granule during the repeated exertion and reduction of force on the granule, repeated compression characteristics about the granule can be obtained and may be useful in evaluating the fitness of the granule for certain applications. Recorded results can be analyzed and compared with recorded results obtained from substantially identical testing on granules with known repeated compression test characteristics. In real-world applications where a standard previously-tested granule exhibits acceptable properties such as breakage strength, a tested granule that exhibits similar repeated compression test results could be likewise considered acceptable for similar applications.

According to the present invention, the compression test apparatus shows improved spatial resolution by using a double spring technique. According to the present invention, variables are controlled that are especially important during the development of the first cracks in the particle and the extent to which the breakage process occurs. This breakage control is achieved by an automatic reduction of compression force during the breakage process. The magnitude of the reduction is determined by the apparatus and is proportional to the extent of granule collapse during the breakage process. For example, a reduction that shows good results is approximately 40 mN/$\mu$m of granule deformation, which means that if the granule diameter, as measured between the contact surface of an indentor and the contact portion of a platform, or between two parallel plates, decreases 10 micrometers due to the development of a large crack, the compression force on the granule is directly reduced by 0.4 Newton. For granules with a breakage force of, for example, between 0.5 and 5 Newton, this reduction according to the example would be sufficient to stop the breakage process. It even allows monitoring brittle breakage by crack development at different stages of the crack development process.

The compression system nearly always acquires a new steady state within a fraction of a second. In this state the reduced granule strength, due to for example a crack formation, is still large enough to withstand the strongly reduced compression force. For the granule to collapse completely, the (fast) cycles of compression, crack development and force reduction continue until the cracks have fully developed and the granule is broken, or until the granule has flattened extensively by plastic deformation.

As shown in FIG. 1, a double spring compression test apparatus according to the present invention is provided and includes a bottom plate 20, a platform 22, a bottom biasing member 24 in the form of a coil spring, an indentor 26, and a top biasing member 28 in the form of another coil spring. The bottom plate 20 has a top surface 30 that contacts, or, as shown, is connected to, a lower end 32 of the bottom biasing member 24. The platform 22 includes a top surface 34 and an opposite bottom surface 36 that contacts or, as shown, is connected to, an upper end 38 of the bottom biasing member 24. The platform top surface 34 has a biasing portion 40 and a contact portion 42 for contacting a granule to be tested. The indentor 26 has an indentor bottom surface 44 and a contact surface 46. The top biasing member 28 has a lower end 48 that contacts, or, as shown, is connected to, the biasing portion 40 of the platform top surface 34. The top biasing member 28 also has an upper end 50 that contacts, or, as shown, is connected to, the indentor bottom surface 44.

FIGS. 2A and 2B depict another embodiment of the present invention. As shown in FIGS. 2A and 2B, the apparatus of the present invention includes a bottom plate 60, a platform 62, a bottom biasing member 64 in the form of a Z-spring, an indentor 66, and a top biasing member 68 in the form of another Z-spring. The bottom plate 60 has a top surface 70 that contacts, or, as shown, is connected to, a lower horizontal arm 72 of the bottom biasing member 64. The platform 62 includes a top surface 74 and an opposite bottom surface 76 that contacts or, as shown, is connected to, an upper horizontal arm 78 of the bottom biasing member 64. The platform top surface 74 has a biasing portion 80 and a contact portion 82 for contacting a granule to be tested. The indentor 66 has an indentor bottom surface 84 and a contact surface 86. The top biasing member 68 has a lower horizontal arm 88 that contacts, or, as shown, is connected to, the biasing portion 80 of the platform top surface 74. The top biasing member 68 also has an upper horizontal arm 90 that contacts, or, as shown, is connected to, the indentor bottom surface 84. In FIGS. 2A and 2B, it can be seen that the indentor 66 is of a two-part construction and includes a top plate portion 92 and a contact member portion 94 secured together as, for example, by welding. Strain gauges 96, 97, 98, and 99 can be seen on the middle, diagonal arm of each respective Z-spring. A force exertion or force-generating device 95, such as a hydraulic press plate or piston, is shown positioned above the apparatus.

FIGS. 3A and 3B illustrate yet another embodiment of the apparatus of the present invention. The embodiment of FIGS. 3A and 3B is similar to the embodiment of FIGS. 2A and 2B with the exception that a height adjustment screw 100 is provided to maximize the operational range available due to high pre-load values. In addition, a support unit 102 is provided as part of the platform top surface and provides the contact portion 104 of the platform 106. According to this embodiment, the indentor 108 includes a top plate 110 and the adjustment screw 100. As can be seen in FIGS. 3A and 3B, the granule 112 to be tested is positioned directly beneath the adjustment screw 100. By using a force-generating device 114 having a sharp tip, and providing a small centering hole or dimple 116 in the top surface of the indentor, the force-generating device becomes self-centering and ensures that no moment is added to the system from the top.

An important feature of the apparatus is the platform, which is situated between the indentor and the bottom plate. By the design of the top and bottom biasing springs, the platform will move in parallel towards the bottom plate whenever the indentor is moved. If a granule is placed between the platform and the contact surface of the indentor, it will be deformed with a distance u. This distance is much smaller than the distance the indentor has moved, because the platform has also been pushed downwards. By using a properly designed Z-shaped spring it is possible to create a system that guarantees very good parallel guiding with extremely low tolerances. These Z-shaped springs are preferably equipped with strain gauges, which measure the deformation of each of the springs. As long as the spring is deformed elastically, the force acting on the spring follows from Hook's law. These springs are commercially available with strain gauges and temperature compensated electronics. By measurement of the deformations of both springs, simultaneous measurements of the force on and deformation of the particle are obtained.

The spring parallel to the granule allows determination of the indention of the particle, as it is deformed over the same distance. The total load on the construction is determined by the strain gauges on the bottom spring. The force on the granule follows directly from the difference between the total force and the force parallel to the granule.

An XY recorder can be applied directly to the terminals of the load cells. The X-channel measures the signal of the strain cell parallel to the particle, which equals the deformation of the particle. The Y-channel measures the voltage between both positive ends of the strain cells. The latter signal is directly proportional to the difference between total force and the force parallel to the granule, which means it is proportional to the force on the granule.

Provided that no moments are exerted to the apparatus, the stiffness of the support unit that compresses the circuit of load cells is unimportant. This has the advantage that the construction can be of any material, with the restriction that as little moment as possible should be exerted on top of the system. By attaching a very thin connection piece at the bottom, the moments exerted on the apparatus can be reduced substantially. By using a sharp indentor on top of the support unit and preparing a small hole in the contact plane, the indentor will become self-centering, and ensures that no moment is added to the system from the top.

Under some circumstances, the range of operation of the apparatus may be limited by both loads of the loading cells. In particular, the total force on the particle and on the spring in parallel with the particle should not exceed the linear range of the force transducers used. Therefore, the maximum allowed force on the bottom cell should not exceed, for example, 20 Newtons. The maximum breakage force that can be measured with an apparatus of such construction is preferably about 15 Newtons, because the operational range of the bottom spring has to include the force parallel to the particle. Other load cells can be used when different forces are necessary to break or compress particles.

When the granule has to be approached over a large distance by the cells, both the bottom and the top load-cells will take considerable pre-load values, even before a granule is stressed. This significantly reduces operation range. To compensate, an extra height adjustment screw may be added to avoid small operation ranges due to high pre-load values. This screw moves the indentor very close to the particle prior to compression testing, and has the advantage that the entire operation range is always available for particle loading.

To facilitate granule loading and to allow accurate granule positioning, the indentor screw can easily be removed and temporarily replaced with a specially constructed small funnel that just reaches the bottom of the anvil. Particle positioning is as simple as throwing a single granule in the funnel. After carefully removing the funnel, the height adjustment screw is replaced and adapted to be in close range.

Another advantage of using a funnel for particle loading is that it can be done without touching the granules. Some granules already suffered damage upon catching them with a pair of tweezers. Therefore granule handling was performed only with paper tweezers and the use of the funnel.

When a particle in this new compression test apparatus is loaded beyond its point of breakage, the actions of both springs will start reducing the load on the particle very rapidly. Initially, the bottom spring will move the platform upwards, as the force balance around the platform is disturbed. Upon deformation of the particle, the top spring becomes compressed more extensively, thus taking a higher load. This way the force balance around the platform is rapidly restored, while the damaging force on the granule is reduced very quickly (in a few milliseconds).

The compression apparatus of the present invention forms a mass-spring system with a reaction time according to the formula $$\tau = \sqrt{m_{eff}/(C_1+C_2)}$$

where $\tau$ is the cycle time of the resonance frequency of this mass spring system, $m_{eff}$ is the effective mass of the moving mass, and $C_1$ and $C_2$ are the spring constants of the bottom ($C_1$) and top ($C_2$) springs.

For a spring constant of the order of 33 Newton per millimeter and for moving parts that have a joint weight of 430 gram, this results in a resonance angular velocity of 392 rad/s or about 62 Hz in the absence of a particle. This means that a typical reaction time of the system would be 16 ms as compared to a few hundred ms for prior devices. As a consequence, the present apparatus shows a much better semi-statically approximation compared to the performance of, for example, the compression test apparatus described in the article of A. Reetz: Granulatfestigkeits-Prufung, Materialprtifung 33, 7–8 (1991) page 219–222. The effective stiffness of the whole apparatus easily doubles if a granule is present. This results in even shorter reaction times, provided that the particle is not broken.

There is always some force that remains applicable to the granule and this ensures that the granule cannot rearrange to another position during the breakage process. Such a guarantee is important, as otherwise particle reorganizations can make interpretations of stress strain curves much more difficult. When compared to constant indentation increments, or to constant force increments, the first figure gives the most extensive information about the breakage process.

With the double spring apparatus of the present invention, granules are smoothly deformed even after initial breakage. Smashing of the granule is avoided by the reduction in the compression force that occurs automatically during the breakage process.

EXAMPLES

Several types of granules were used to compare the suitability of different compression tests: fluid bed granules 1A and 1B, high shear granules 2A, and granule 3—the spherical prill particle.

four types of granules were tested: fluid bed process granules, high shee r process granules, prilling process granules, and extrusion process granules. The fluid bed process granules were produced as follows.

1A) A granule based on a core of sodium sulphate (directly mined) and coated with an enzyme and a cellulosic coating: the core material consisted of irregular shapes because the required size distribution had been obtained by sieving and recycling. The granules further consisted of an enzyme layer and a cellulose and cellulose ether coating. Typically the amounts of cellulose and cellulose ethers were 40% cellulose, 30% HPMC and 30% HEC (hydroxy ethyl cellulose).

1B) A granule based on a core of sodium sulphate that had been re-crystallized to improve the sphericity. This core was coated with an enzyme and cellulose coating. The composition of this granule was the same as 1A.

1C) A granule based on a composite salt core. This salt core consisted of a small sodium sulphate seed that had been coated with an ammonium sulphate coating. This layer of ammonium sulphate created a more spherical core, which was coated with an enzyme and an ammonium sulphate. Finally a methylcellulose (MC) coating layer had been added to this granule.

1D) A granule based on a nonpareil type A core. Around this core material an enzyme and an ammonium sulphate layer had been added. Finally a layer of MC(methylcellulose) had been added to this granule. The production of this granule was similar to that described in Patent Publication WO 93/07263 (Genencor International 1993).

The nonpareil core material used in fluid bed trials is a commercial product (also called Nu-core™) that is available in several grades (designated herein as A and B), depending on size and outer coating. These spherical particles have been produced in a pan agglomeration process with sugar, starch, and PVA.

Granules that were produced in a high shear granulation process were as follows. p1 2A) The patented and commercially available high shear enzyme granule from Novo Nordisk in Denmark also called T-Granule. These granules contain cellulose fibers that improve their mechanical behavior. These granules were made using a high shear granulator (for example of the Lödige type). A typical composition is given in the Hove Nordisk European Patent No. 0170360 (1986). These granules were coated with about 10–15% of polyethylene glycol (PEG) with $TiO_2$ added as pigment.

2B) These are similar to 2A, but with the addition of artificial fibers such as PEG. They are described in Showa Denko's European Patent No. 0256127 (1986).

Granules that were produced using the prilling process were as follows.

3) This granule was made using a process wherein a molten mixture of polyethylene glycol (PEG) sodium sulphate and a dry enzyme powder are dispersed in air through a nozzle. The droplets solidified in the air producing very spherical particles. They were coated with 2% waxy material (1:1 mixture of glycerol mono stearate and paraffin) and afterwards about 2% of aerosil (silicon dioxide) was added in order to enhance flow characteristics. This type of granule is called a prill.

A fourth type of granule, the extrudate, was added to illustrate the effect of their irregular shape. Small-scale test batches were available for this type of granule. The granulates were extruded by means of a screw pump, which pressed a mass through small dies. The resulting strings were then broken into granules in a second operation. The extrudate granules were as follows.

4A) Non spherical extrudate chops. A mass containing carbohydrates and enzyme powder was extruded and the strings that were milled in order to obtain a suitable particle size distribution. Non-spherical granules were produced. This batch was deliberately not spherized.

4B) Cylindrical extrudates. These particles were produced according to U.S. Pat. No. 4,242,219 (1980). The strings were cut into cylinders using sharp knives that rotate just in front of the extruder head. They had a length to diameter ratio of approximately unity. The granules expanded upon leaving the extruder, which resulted in a granule surface without sharp edges.

These various granules were not only manufactured by different processes but also had different compositions. Thus, the differences in the dusting behavior cannot be ascribed to a single cause. Nevertheless, the set of granules illustrated the state of the technology well.

COMPARISON EXAMPLE 1

DIRECT COMPRESSION TESTS (Constant Indention Speed)

Particle strength analyses on the above-mentioned particles were performed with a conventional piston-driven particle compression test. For three different types of agglomerates a large number of reproductions was performned to obtain the particle strength distribution. For each type, 400 experiments were performed in order to obtain smooth distributions.

The distribution functions have been obtained by plotting the number of granules breaking in a force class of 0.1 N width. As the accuracy of the force measurement used in the apparatus was 0.1 mN, it is clear that the resulting distributions are characteristic for the particles and their orientation in the current apparatus. The orientation effects of non-spherical, non-homogeneous particles are difficult to understand. Different contact areas between the particles will be responsible for part of the spread in results.

A simple method to assess the width of the distribution is to determine the standard deviation. For the interpretation of the results shown in Table 1 below, it is important that it is not an estimate of the error in the results; therefore even results that show very high (relative) spread can be meaningful.

TABLE 1

Measured average breakage force and standard deviation from 400 compression tests with a Zwick set-up for fluid bed granules (type 1-A and 1-B) and prill particles (granule 3).

|  | N [#] | $F_b$ [N] | σ [N] | $σ/F_b$ [—] |
|---|---|---|---|---|
| Granule 3 (prill) | 400 | 1.1 | 0.2 | 0.2 |
| Granule 1-A (fluid bed) | 400 | 2.1 | 1.2 | 0.6 |
| Granule 1-B (fluid bed) | 400 | 2.7 | 0.7 | 0.2 |

The apparatus used to test these agglomerates encountered several problems. First of all, the spatial resolution did not allow monitoring of the breakage process. It did especially not allow any discrimination between brittle or plastic failure. Often when a particle starts yielding, the measured force can increase significantly during this failure process. So when comparing a quite strong but brittle particle with a plastic yielding agglomerate, false conclusions could be drawn about granule strength.

The second problem is that it takes a lot of time to generate a reliable particle strength distribution. The slow compression process itself consumes an important part of this time. The manual loading of particles in the apparatus causes another important part of this requirement.

Automation of the apparatus does not necessarily make particle compression testing a useful test. First of all, it will not make the determination of particle strength a fast method, as still a large amount of time is required to compress the granules. Secondly, the results of detergent granules show a very wide strength distribution, and a comparison of strength of different types of granules will result in distributions with a large similarity and much overlap.

COMPARISON EXAMPLE 2

DIRECT COMPRESSION TEST (Constant Force Increments)

As a test, a series of experiments was conducted in the constant force increment mode, using a commercially available (Etewe, Germany) completely automated set-up for granule compression testing. In this fully automated compression test set-up, a digital camera first makes a picture of a whole sample of granules. For an individual granule, the position and particle cross section is determined with the help of image analysis. Afterwards, a computer algorithm moves the indentor to just above the particle and starts a compression experiment. When data of the particle compression experiment is obtained, the indentor is moved towards a special cleaning area, which prepares the indentor for the next particle. Results were analyzed for particle breakage phenomena by an algorithm that scans for the first (major) reduction in compression force.

For a series of 13 experiments with prill particles (granule 3), the mean of the breakage force equaled 1.4 N and the variance equaled 0.23. If this result is compared to the compression strength distribution of the prill particles, it appears that there is some effect of the different types of equipment use to obtain the force displacement curves, but the results do not differ very much. lo The particle compression results show a wide distribution, and the results from the constant force increment method agree with the constant indention force method. However, both methods result in a large variation in outcomes, which makes granule strength assessment and comparison of enzyme formulations very difficult.

EXAMPLE 1

DIRECT COMPRESSION TEST (Double Spring Method)

In FIG. 4, the stress strain curve for a prill particle has been obtained using the double spring method. The effect of particle size was eliminated in these experiments by means of a carefully collected sieve fraction. Usually some particles get stuck in the sieve after sieving, and these particles are in a very close size range. After just tapping once on the sieve, the particles were liberated and could be collected. This way, a very narrow size distribution was achieved (about 690–710 um). An example of a force displacement curve for high shear granule 2-A particle is given in FIG. 5. This granule does not show an easily determined point of breakage; instead it will deform plastically. Nevertheless, the force was determined. This characterizes the maximum load on the particles where the particle still behaves elastically. In FIG. 5, this point was determined by fitting a linear line along the initial elastic behavior of the granule and estimating the indention at the moment when strong deviations (larger than 5 percent) were observed from this linearity.

Discussion

A fundamental problem of particle compression experiments is the large variation in results. From an experimental comparison of at least 400 granules a large distribution in breakage strength is observed. In the direct compression experiments the orientation of even a spherical granule generates part of the distribution in breakage results, as the granule is not always loaded at its weakest spot. Differences in compression strength results from different types of granules are small compared to observed variations in results for a single type of granule. Therefore, the single particle compression test is of limited value for understanding the mechanical quality closely related to types of granules.

The amount of information about granule breakage strongly depends on the compression method used. A new method has been proposed to optimize the information obtained from the breakage process. For some types of granules visible crack development and force displacement curves are directly related. Variations in force displacement curves can therefore be interpreted as variations in the development of cracks.

The types of breakage mechanisms are very different from one another. Curves showing a sudden drop in force and increases in deformation indicate a sudden point of breakage, whereas curves only showing a smooth process of deformation and indicate plastic deformation of the granule. By determining the discontinuity in force and sudden displacement at the point of breakage, this difference in behavior is characterized. The dynamics of the breakage process are related to the dynamics of the load cells. This can directly be seen in FIG. 6 wherein the drop in force is plotted as a function of increase in deformation. FIG. 6 shows a determination of the relationship between observed drop in force ($\Delta F$) and step in deformation upon breakage ($\Delta u$) caused by the load cell set-up. The ratio of the drop in force and the increase in deformation is apparently constant and is a test machine property, which depends on the stiffness of both springs. Therefore granule breakage behavior can be either quantified with a drop in force or with an increase in deformation. The magnitude of both the drop in force and the increase in deformation is related to the mechanism of particle failure. Brittle breakage is represented by points on a graph with significant steps in force and displacement, while nearly plastic deformation is associated with a near absence of those steps.

To determine the extent of plastic deformation during breakage, the drop in compression force needs to be compared to the absolute force of breakage. For understanding the mechanisms, results from differently behaving particles need to be compared. The results from the set of eight types of fluid bed formulations have been analyzed for this reason. Data sets obtained with eight types of fluid bed formulations were analyzed in detail, as these results show strong coherence. These granules were all built around a core of approximately 450 $\mu$m and had, when all layers had been added, a particle size of approximately 600 $\mu$m. The computer program was used to determine the breakage of the granules and the extent of brittle fracture. For each layer of the fluid bed formulations, a series of force displacement curves was analyzed. By plotting the results from intermediate products into a single graph, insight was obtained into the mechanical behavior of the different layers of a granule. This way, a characterization was obtained. In graphs, both the breakage force and the observed force drop during breakage can be is presented. The first three experiments have been performed with granules P-A/P-C. Results in Table 2 below show that different core materials had different effects on the breakage behavior of the granules.

TABLE 2

Effect of core material (yielding, plastic compacting, elastic) on the force displacement curves: yielding cores result in weak granules (A) whereas an elastic core results in the strongest particles (C).

| | | type P-A non-pareil | | | type P-B salt core | | | type P-C Na$_2$SO$_4$ core | |
|---|---|---|---|---|---|---|---|---|---|
| | $F_{brk}$ [N] | $\sigma$ [N] | $\Delta^f$ [N] | $F_{brk}$ [N] | $\sigma$ [N] | $\Delta^f$ [N] | $F_{brk}$ [N] | $\sigma$ [N] | $\Delta^f$ [N] |
| Core | 0.84 | 0.24 | −0.44 core | 0.99 | 0.6 | −0.73 core | 1.98 | 0.91 | −0.56 |
| PVA- | 1.25 | 0.65 | −0.31 PVA- | 1.99 | 1 | −0.35 PVA- | 3 | 1.45 | −0.09 |

TABLE 2-continued

Effect of core material (yielding, plastic compacting, elastic) on the force displacement curves: yielding cores result in weak granules (A) whereas an elastic core results in the strongest particles (C).

| | type P-A non-pareil | | | | type P-B salt core | | | | type P-C $Na_2SO_4$ core | | |
|---|---|---|---|---|---|---|---|---|---|---|---|
| | $F_{brk}$ [N] | σ [N] | $Δ^f$ [N] | | $F_{brk}$ [N] | σ [N] | $Δ^f$ [N] | | $F_{brk}$ [N] | σ [N] | $Δ^f$ [N] |
| talc Enz | 1.54 | 0.45 | −0.31 | talc Enz | 2.14 | 0.62 | −0.35 | talc Enz | 5.8 | 3.33 | −0.09 |
| AS | 1.44 | 0.2 | −0.76 | AS | 2.66 | 0.82 | −0.87 | AS | 4.13 | 1.39 | −0.19 |
| PVA-$TiO_2$ | 1.26 | 0.51 | −0.16 | PVA-$TiO_2$ | 3.12 | 0.91 | −1.08 | PVA-$TiO_2$ | 3.39 | 2.33 | −0.08 |

Tests show that a very weak and flexible nonpareil core fails at forces just above 0.8 Newton. Polyvinyl alcohol (PVA) coatings around the core increase the strength of the granule. Application of more layers does not result in any more improvement, suggesting that failure of the core determines the strength of the granule. More rigid and stronger core material composed of an ammonium sulphate (AS) coated sodium seed results in a much stronger granule. The addition of an enzyme layer (Enz) around this seed does not result in any change in behavior, suggesting that the enzyme layer behaves as a passive rigid layer. Addition of the ammonium sulphate (AS) layer results in a much larger deformation before breakage, and increased granule strength. This suggests that the ammonium sulphate layer redistributes the force on the granule over the whole granule core. As the outermost layer of the core material also consists of ammonium sulphate, it is not surprising that the ammonium sulphate only exerts forces on the core that it can handle.

Results for a granule that consists of a sodium sulphate crystal core show the largest strength, while being quite stiff. The addition of a polyvinyl alcohol (PVA) coating even further increases the strength of the granule. Possibly, the cushioning effect of the polymer layer helps the granules to avoid too much stress on weak crystal edges. The addition of an enzyme layer shows also a significant increase in granule strength. However, addition of an ammonium sulphate layer that is brittle results in decreased granule strength. Possibly, the crystal structure of the ammonium sulphate influences the enzyme layer in such a way that it again can damage the core material, right through the PVA layer.

The effect of granule geometry on breakage strength is shown by comparing a granule composed of a thick enzyme and coating layers with a granule that has two enzyme layers, each of which is protected by its own coating. Layer thickening hardly influences granule strength whereas a layered structure improves granule strength as shown in Table 3 below.

TABLE 3

Effect of different coating geometry (the same amount of coating added as a single layer around a particle or added as two concentric layers) on the force displacement curves for layered enzyme granules: layer thickening hardly influences granule strength (P-D) whereas a layered structure improves granule strength (P-E).

| | type P-D thick layers nonpareil | | | | type P-E lammellar salt core | | |
|---|---|---|---|---|---|---|---|
| | $F_{brk}$ [N] | σ [N] | $Δ^f$ [N] | | $F_{brk}$ [N] | σ [N] | $Δ^f$ [N] |
| core | 0.85 | 0.62 | −0.42 | core | 0.85 | 0.62 | −0.42 |
| Enz(1) | 1.09 | 0.8 | −0.39 | Enz(I) | 1.29 | 0.49 | −0.29 |
| Enz(2) | 1.09 | 0.89 | −0.39 | MC(1 | 1.66 | 0.49 | −0.29 |
| MC(1) | 1.67 | 1.36 | −0.05 | Enz(2) | 1.01 | 0.47 | −0.11 |
| MC(2) | 1.54 | 1.55 | −0.06 | MC(2) | 2 | 0.84 | −0.12 |

From Table 3, the effect of the thickness of the enzyme and coating layers is easily recognized. After addition of the usual amount of enzyme material, the strength of the granule is clearly increased. The addition of even more enzyme material hardly changes the breakage force. The addition of a methyl cellulose coating (MC or MC-coating), however, results in a strong increase in breakage force. Again doubling the MC-coating layer thickness hardly increases the breakage force.

After addition of coating material, the breakage force of the granule is strongly increased. Addition of a second layer of enzyme material around the coating reduces the ranule strength. Addition of yet another coating around this second layer increases the strength of the granule even more. For a layered granule the resulting granule strength is larger, even when exactly the same amount of material is used in the granules.

The effect of internal structure is further studied by comparing granules in which brittleness is varied by either the addition of polymer layers between successive layers, or by the mixing of enzyme and ammonium sulphate layers, as shown in Table 4 below.

TABLE 4

Effect of the enzyme/ammonium sulphate interface on the force displacement curves: The highest granule strength is obtained with a yielding/plastic interface and results in a strong flexible particle (P-H); an interface between a yielding layer and a brittle material appears weak (P-G).

| | type P-F extra PVA-TIO layer | | | | type P-G mixed Enz | | | | type P-H mixed AS | | |
|---|---|---|---|---|---|---|---|---|---|---|---|
| | $F_{brk}$ [N] | σ [N] | $Δ^f$ [N] | | $F_{brk}$ [N] | σ [N] | $Δ^f$ [N] | | $F_{brk}$ [N] | σ [N] | $Δ^f$ [N] |
| core | 1 | 0.69 | −0.41 | core | 0.85 | 0.62 | −0.42 | core | 0.85 | 0.62 | −0.42 |
| Enz | 1.29 | 0.49 | −0.29 | Enz/AS | 1.23 | 0.55 | −0.36 | Enz/AS-1 | 1.23 | 0.55 | −0.36 |
| PVA-TiO$_2$ | 1.31 | 0.83 | −0.29 | AS | 1.17 | 0.56 | −0.36 | PVA-talc | 1.35 | 0.85 | −0.36 |
| AS | 1.53 | 0.37 | −0.08 | MC | 1.2 | 0.55 | −0.16 | Enz/AS-2 | 1.84 | 0.92 | −0.63 |
| MC | 1.96 | 0.97 | −0.09 | | | | | MC | 2.57 | 0.79 | −0.46 |

The first column of results in Table 4 shows that addition of the ammonium sulphate around a nonpareil core, which itself has been coated with an enzyme and a PVA-TiO$_2$ layer, only slightly increases granule strength, but maintains the granules' large flexibility. The ammonium sulphate layer that has been added on top of the PVA-TiO$_2$ layer results in plastic failure. This is in contrast to P-A/P-C where the ammonium sulphate added on top of an enzyme layer had the opposite effect. Addition of an extra MC layer does increase granule strength.

The second column of results in Table 4 shows a granule that consists of a nonpareil core that is coated with a mixture of enzyme followed directly by an ammonium sulphate layer. Addition of an MC coating layer hardy increases the strength of this particle. Apparently the enzyme ammonium sulphate layer controls the characteristics of the particle.

The most interesting column of results in Table 4 is the third column. The third column of results shows the results of a granule that has been designed to deform plastically. To do so, its ammonium sulphate layer has again been mixed with the enzyme layer and it has been added in two layers, separated by a PVA-coating. This assures that any cracks that occur during plastic deformation have to pass an elastic polymer layer before reaching the other enzyme/ammonium sulphate layer. The PVA-TiO$_2$ coating only slightly improves the strength of the first enzyme ammonium sulphate layer whereas that addition of the second enzyme/ammonium sulphate layer and the MC coating significantly improves granule strength.

While particle compression experiments are easily conducted, the results are hard to compare, especially when similarities among different types of industrial granules are very large. The double spring device makes the deformation process and the type of breakage (brittle or plastic) clearly visible.

For a selected set of fluid bed granules, the differences between breakage force and elasticity have been observed. For such a type of granule the following observations have been made:

the type of core material is very important for the resulting granule compression strength;

a lamellar granule design results in superior granule strength;

an enzyme/ammonium sulphate layer can result in very weak or very strong granules, depending on the protective coating layer, suggesting that an enzyme/ammonium sulphate layer can yield plastically and that a polymer coating helps to avoid this.

In another embodiment of the present invention, an apparatus according to the present invention, for example, any of the double spring apparatus shown in FIGS. 1–3B, can be used to conduct repeated compression testing.

In the direct compression experiments described above, it was difficult to distinguish between plastic and elastic deformation of a granule. Only during granule breakage could some information about the behavior of the granule be obtained. More information can be obtained about plastic deformation of a granule by carefully compressing and relaxing the granule by way of a repeated compression test according to the present invention.

Repeated compression tests performed using the double spring apparatus result in graphs that show that granules tested can be compressed to a maximum force of 0.5 N without breakage. When this force is electronically detected, the motor that drives the compression is stopped and reversed in direction. The motor then decreases the load on the granule to below 0.05 N, and prepares for the next cycle by again changing the direction of the motor. The granule is ten times tested at each compression level. If the granule survives the first series of cycles without breakage, a second series is executed with a maximum force of 1.0 N. If the granule has not broken, it is subjected to a third series with a maximum force of 1.5 N. If after these repeated compressions the granule still survives, the force limit is removed and the granule is compressed until breakage is observed.

The electrical control for repeatedly compressing the granules is very simple. The electronics need to change the polarity of the motor driving the compression, depending on the magnitude of the force exerted on the granule. To realize this, two comparator integrated circuits are used. The first comparator checks for the manually pre-set maximum compression force. If the force exerted on the granule exceeds this value, the positive signal of the comparator is translated into a change of the movement direction of the force-exerting or force-generating device. The second comparator assures that the force-exerting device can only be retracted if the force on the granule is at least 0.05 Newton. If it becomes smaller, the system switches the direction again. The force-exerting device then restarts to compress the granule and the next cycle begins.

The change between the different levels is conducted manually. After ten compressions at 1.5 Newton, the change in direction is overruled and the apparatus starts breaking the granule.

The used load cells should under no conditions experience forces that exceed 20 Newtons. To avoid this, a simple, but effective protection has been achieved by adding a set of electrical comparators to the apparatus. The comparators check whether the output voltages of any of the load cells exceed 9.95 Volts, as this corresponds to 19.9 Newtons. If any of the comparators results in a positive voltage, this is electronically translated into stopping the movement of the indentor immediately.

The number of repeated compression cycles are chosen in such a way that fatigue effects can be expected. The compression cycles in the repeated compression tests have been repeated ten times in order to resemble the fatigue behavior achieved from repeated impacts as achieved with a device as described, for example, in U.S. Pat. No. 6,035,716, which is incorporated herein in its entirety by reference.

The maximum compression force used during the compression cycles (e.g. 0.5, 1.0 or 1.5 N) is based on the maximum impact test. The granules tested in the repeated impact machine have a diameter of approximately 500 micrometers, a density of approximately 1.2 mg/mm3 and an average particle mass of approximately 0.1 -mg. The impact velocities in the impact test range up to 10 m/s, so the maximum kinetic energy of the granules in the test is of the order of 5 micro Joule. For granules of a stiffness of approximately 0.2 MN/$\mu$m, the maximum indention approximates 10 $\mu$m and the maximum force 1.5 Newton. To resemble the conditions in the repeated impact machine, the maximum forces in the repeated compression test have also been chosen at 1.5 N.

The number of collisions a granule can survive without breakage can be determined by using the repeated impact machine of U.S. Pat. No. 6,035,716. The effect of impact energy is much stronger than the effect of fatigue: a thirty percent increase in impact velocity corresponds with a fivefold reduction in the number of collisions a granule survives. For this reason it can be expected that if the maximum compression force is strongly increased (50% or more), the effect of previous compression cycles at much lower maximum force can be neglected. Therefore fatigue effects from repeated compression cycles at 0.5 N are not expected to influence those carried out with higher maximum forces.

Many of the compression curves show hysteresis, which means that the total energy under a loading force displacement curve is larger than the total energy under an unloading curve. The difference between those energies is the amount of energy that is transferred into heat or into damage inside the granule. This is therefore an interesting quantity that gives information about the particle breakage process.

The most characteristics points on a hysteresis graph are easily identified as the start of each loop (Left, L), the top of each loop (T), the rightmost point (R) and the end of each loop (E). By identifying for each of these points deformation and observed force and time dependency, nearly all information of individual loops can be retrieved later. By determining the top, right and end of each loop relative to the beginning of it (left), the observed values can be compared within a measurement and statistically evaluated.

A computer program has been developed, capable of automatically analyzing these curves. It is capable of determining all interesting quantities from a thorough analysis of the curves. Apart from each of the characterizing points of a cycle, it also determines the point of breakage, the absolute maximum force and the largest drop in force. The program determines both the left and end point of each loop by first identifying the slopes running down from the top and right point. Afterwards it determines the left and end point at 0.05 Newton of force.

Distributions of energy recovery rates in the compression test have been determined, but results are strongly influenced by the time dependency of the granule deformation recovery. This can be seen in the next compression curve, which is performed after significant delay, that always starts much earlier than can be expected from the previous curve. Apparently, some residual energy remains in the granule.

A great deal of information can be obtained about the behavior of spherical particles in a compression test by means of very simple experiments. Of course the simplest case and easiest way is to use a perfectly spherical and homogeneous particle, such as a small glass sphere. The advantage of working with such a type of granule is that behavior can be theoretically predicted. The theory for the homogeneous spherical case, which has many industrial applications such as the size of ball bearings, is already very old, and has originally been developed by Herz and discussed in Herz, H. J., reine Angnew. Math. 92, page 156 (1881).

A typical direct compression curve for a glass bead shows that the bead behaves almost perfectly elastically, because after a compression experiment the granule is neither broken nor visibly deformed. The maximum force on the bead is limited by the design of the apparatus to 15 N. It can be seen that hardly any hysteresis is present and that an apparent strong non-linear behavior is characteristic for elastic spheres. The maximum force for the glass bead has been up to 15 N, which is much more than used in experiments with the granules. Nevertheless, the maximum deformation was only 20 $\mu$m, which is much less than in experiments with granules, indicating that the glass bead is a very stiff particle.

Results for perfectly elastic spheres can be extended to more complicated particles such as coated spheres, by a simple experiment with a thin sheet of paper. Results from an experiment where a single 90 $\mu$m paper layer was placed below a glass bead show that the stiffness measurement has been reduced and that now hysteresis occurs. Adding a second paper layer results in a different hysteresis pattern and in an even more reduced stiffness.

A small layer can have a huge effect on the stress-strain curve of the final granule. The thin piece of paper deforms much more than the remainder of the particle, because the glass sphere has a larger stiffness than the paper. Another reason for the larger deformation of the paper layer is that it experiences the highest stresses. The relatively small paper layer has a much shorter distance to the contact area than the glass interior of the sphere, which makes its deformation larger.

These results help the interpretation of stress-strain curves of layered granules significantly. If the overall stiffness of a granule is decreased by the addition of an extra layer and the force-deformation diagram shows a non-linear compression, it can very likely be contributed to the outermost layers.

EXAMPLE 2

Results from experiments with several types of (industrial) enzyme granules are given below. Typical stress-strain curves obtained by repeated compression measurements of a spherical enzyme-containing granule (prill granule) are shown in FIG. 7. FIG. 7 shows how the granule is first compressed for ten times at a quite low force level (0.5 N), and thereafter ten times at 1.0 N. During the start of the third series at 1.5 N the granule shows breakage and splits in a very regular way as is visible in photomicrographs.

In FIG. 8, the three phases of a force displacement diagram of a repeated compression experiment can be recognized. In Phase A, the force displacement curve indicates that the particle is elastically loaded close to the point of breakage and indicates that some cracks have formed due to the repeated loading cycle, but they have not extended throughout the granule. In Phase B, that occurs directly after breakage and nearly instantaneous with the propagation of a few cracks, cracks extend over the whole granule surface. In Phase C, after continuing the compression, the cracks grow and extended particle deformation is observed. It can be seen that the breakage process itself can be studied and that different stages of breakage show strong correspondence among the same type of granules.

Most other enzyme granules of interest are much less spherical and show larger differences in size. Nevertheless, the breakage process can be monitored accurately with this test for spherical particles.

Another interesting series is shown by compression curves of high shear granule 2-A particles. Results from compression tests on a granule-T with a diameter of approximately 800 micrometers show that the particles do not seem to collapse under the compressive forces tested, but they clearly deform as a result of the loading. A large spread in initial plasticity is observed. This can be explained by assuming an a-spherical shape. Depending on the area exposed to the compressing plates, the a-spherical particles will encounter a different stress and, associated with this, a different level of compaction. Granules having fibers incorporated in the granule do not show brittle failure.

Brittle breakage shows a sudden damage to the granule. The opposite is a continuous damage, such as plastic yielding. From this understanding, it can be understood that the high shear granule 2-A deforms plastically because hardly any drop in force can be detected, while a prill particle keeps its shape for a longer time but suddenly fails after which a clear drop in force can be registered.

The maximum deformation in a compression cycle and the amount of plastic deformation that remains after a compression cycle are the parameters that will be used to characterize granule deformation in the graphs of FIGS. 9 and 10 below. For each layer, ten compression cycles have been performed at three different levels of the compression force. The obtained measurements of the plastic deformation and the maximum deformation have all been collected for all compression cycles during typically six experiments. The results inevitably show a distribution in results, both due to differences between different granules and due to the compaction behavior within the measurements to a single granule. The differences within the results from a single granule are larger than those due to the compaction effects within a series. Therefore all results obtained from repeated compression tests at a particular level (e.g. 0.5 N) are treated as a characteristic of the same deformation behavior.

When results from a single compression test are analyzed, one can often see a clear compaction. The first compression cycles result in much more deformation of the particle than the last cycles. After eight or more cycles, the effect of a compression cycle becomes nearly constant.

It is convenient to consider the information of an entire series of compaction tests with the same product, typically six to eight compression experiments, as it appears that the same compaction effect is present in all experiments. The graphs of FIGS. 9 and 10 present the median of the range of plastic and elastic deformations observed and the median of total deformations. This is preferred over the average values as it is less influenced by the strange behavior of granules that already show some breakage during the compression cycles. Results from cycles at different compression forces, i.e., 0.5 N, 1.0 N, and, if still not broken, at 1.5 N, are plotted along a line at slightly elevated positions. The degree to which different lines overlap, or the length of the gap, indicates whether the amount of plastic deformation is larger than the elastic deformation of the granule at a lower compression force. If there is no overlap, the plastic deformation of the granule is apparently more important than its elastic recovery. This is referred to as plastic yielding.

FIG. 9 shows results of a plastic deforming granule (granule-T). It shows a strong permanent deformation during the compression cycles, but also a large elastic deformation. This indicates that the granule does not suffer from cracks that easily grow through the particle, that is, it does not yield, but rather it deforms in a tough and plastic way. This combination results in a large proportion of overlap between different compression cycle lines (P-E lines).

For a set of eight complex multi-layered granules, repeated compression tests were performed using the double spring apparatus. For each type of granule, samples of four or five intermediate products were also tested during the fluid bed coating process. The purpose of this was to obtain insight into the effects of layer additions to the mechanical properties of the granules. For each product six granules were tested with the repeated compression test, if possible, at three different force levels. The first three graphs shown in FIGS. 10A–10C, show the median of the plastic (P) and elastic (E) deformations. For each graph, the left-hand point of each line represents the plastic deformation and the right-hand side of each curve represents the total deformation.

By plotting the results from intermediate products into a single graph, which gives insight into the behavior of the different layers, a characterization of the mechanical behavior of the granule is obtained. Immediately one can see that for nearly all particles and all layers, with an increasing number of layers, the total cycle indentation increases. The same applies for plastic deformation during a cycle. This indicates that all layers deform both plastically and elastically during a compression cycle. Nevertheless strong differences can be seen between granules with different core materials.

From the previously mentioned tests conducted on various types of granules, it can be concluded that the graph of FIG. 10A shows results from a yielding granule. This behavior can be recognized by the absence of data of cycles of the core material, as this granule already starts yielding below 1.0 N. This can also be seen by the fact that the results of compression cycles at increasing force levels do not show any overlap.

The graph shown in FIG. 10B shows the results for the ammonium sulphate coated core, and shows hardly any increase in either plastic deformation or total deformation corresponding to the number of layers. Apparently, the outside layers of the granule become increasingly stiff and strong. This agrees with the conclusions discussed above based on the rigidity of the granules.

The graph shown in FIG. 10C clearly shows a single-crystal core (sodium sulphate) that is surrounded by a number of layers that are deformed significantly more than the core material of the granule. The core, as can be expected, hardly shows any plastic deformation. No yielding is observed, as the results of compression cycles at different compression levels show extended overlap.

The conclusion that can be drawn from the graphs of FIGS. 10A–10C is that the effect of core material is easily recognized in the compression cycle behavior of the granules. A plastic yielding core results in a yielding granule, whereas an elastic and stiff core forces its outside layers to deform. Plastic compacting core material such as used to generate the graph of FIG. 10B is probably most capable of withstanding repeated loads.

In the graphs of FIGS. 10D and 10E, the effect of granule geometry on breakage strength is shown by comparing a granule composed of a thick enzyme coating and coating layers with a granule that has two enzyme layers, each protected by its own coating. In FIG. 10D, it can be recognized that the granule is composed of a core material, two layers of enzyme material and finally two layers of coating material. Apparently the measured plastic deformation and total deformation are hardly influenced by layer thicknesses.

In the graph of FIG. 10E, it can be seen that after addition of the first coating layer, a much more flexible particle is obtained. Addition of a second enzyme layer and a second coating layer results in a particle that shows yielding. From the foregoing discussions, it can be concluded that for the particle breakage force, the layered structure of the granule used to generate the graph of FIG. 10E it breaks at higher force compared to the layered structure of the granule used to generate the graph of FIG. 10D. The graph of FIG. 10E indicates that some yielding of the granule (P-E) during the compression test may have caused this difference.

In the graphs of FIGS. 10F–10H, the effect of the internal structure of a granule is further studied by comparing granules in which brittleness is influenced by varying the distribution of an ammonium sulphate layer over the granule. In this series, the addition of polymer layers between successive layers and the mixing of enzyme and ammonium sulphate layers was tested. The graph of FIG. 10F shows that the enzyme layer shows only plastic deformation, but no yielding. Apparently, the enzyme layer is capable of reducing the yielding behavior of the core. This is in sharp contrast to the enzyme/ammonium sulphate layer used in the graphs of FIGS. 10G and 10H. The enzyme layer is apparently too brittle to reduce the yielding tendency. The PVA-$TiO_2$ coating in the first graph gives rise to some plastic deformation, which is also found in the ammonium sulphate and methyl cellulose (MC) outer coating. The ammonium sulphate layer around the enzyme/ammonium sulphate layer and the MC outer coating in the graph of FIG. 10G reduce the yielding tendency. Direct addition of ammonium sulphate to an enzyme/ammonium sulphate mix does not result in good mechanical behavior, as can be seen from a comparison with the graph shown in FIG. 10H.

The graph shown in FIG. 10H shows the effect of a PVA-Talc coating between the enzyme/ammonium sulphate layer and the outer ammonium sulphate and MC coatings. The graph of FIG. 10H shows large total deformations of the granule and clear plastic behavior, starting with the PVA layer, thus indicating flexible behavior. From conclusions drawn above, it was already indicated that the granule tested to generate the results shown in FIG. 10H is strong and deforms plastically, which agrees with the graphed results.

Highest granule strength is apparently obtained with a yielding/plastic interface and results in a strong flexible particle as shown in FIG. 10H. An interface with a brittle material appears weaker as shown in FIG. 10G.

From the foregoing examples, stress strain data have been obtained for a large set of experimental granules. Analysis of this data is very difficult for several reasons that follow. First, the orientation of the granules in the test apparatus differs. Second, distributions of particle size and shape among the agglomerates concerned can be found between granules, even between those that have been produced in the same batch. Third, a large spread in results of over 50 percent can be encountered; however, since the particles are non-homogeneous and have large size and shape distributions, this can be expected. Fourth, direct measurements often takes a few minutes, while a repeated measurement takes ten minutes. Fifth, each force displacement curve gives a large amount of raw data and requires much effort to analyze.

Statistical reliable information is hard to obtain from the repeated compression curves. For cycle deformation, the $50^{th}$ percentile result gives information about the typical repeated compression behavior of the granule and is not influenced by its original condition. Effects of repeated granule loading, including crack growth or development and fatigue, are expressed in this number. The combination of the total deformation value with the permanent deformation for different layers gives information about the typical mechanical structure of the granule. By the use of this characterization, a fingerprint can be made for typical granule deformation behavior. From the fingerprints many observations can be made.

From the foregoing, it has been determined that granule and plastic deformations increase with an increasing number of layers. In principal, all layers will deform during a compression cycle. The behavior of the core material, for example, the plastic yielding, plastic compacting or elastic behavior, proved to be recognized in the behavior of the final granule. This is in contrast to results obtained from a repeated impact test machine wherein the core material hardly influences end results. By the present test method, the structure of the granule can be recognized in the behavior of individual layers, and it is noted that the addition of coating layers in a lamellar structure results in more plastic compacting behavior.

From the foregoing it has also been recognized that mixing an ammonium sulphate layer with an enzyme layer results in plastic yielding granules. The addition of polymer layers in between such layers increases the flexibility of the resulting granule and decreases plastic yielding behavior.

In conclusion, results of single particle compression tests showed a large fundamental spread in results. For accurate strength distribution assessment, typically about 200 granule compression experiments are preferred. The compression test device of the present invention allowed a detailed study of the breakage process of granules. The apparatus and method of the present invention can also be used to achieve repeated compression curves, which allowed determinations of deformation mechanisms.

The well-defined curves that were obtained with the double spring apparatus of the present invention for a glass bead model particle showed that the dual load cell apparatus was capable of reproducibly measuring load-displacement curves for granules. It was shown that granule breakage processes could be monitored using this apparatus. The brittle breakage process parameters $\Delta F$ and $\Delta u$ as determined in the double spring compression test were related to the stiffness of the load cells. The mechanical configuration ensures a fast load relaxation when the particle broke and allowed extensive monitoring of the breakage process. The magnitude of $\Delta F$ or $\Delta u$ was suitable to determine the extent of brittle breakage of the granule.

In the repeated compression experiments, particles were gradually compressed up to a certain force for ten cycles. The maximum force during granule compression cycles was chosen to resemble conditions of maximum stress in a repeated impact test. Permanent plastic and elastic deformation were used to finger print granule behavior. Granule deformation under certain loads increased with the addition of extra layers around a granule.

For industrial enzyme formulations a number of conclusions were drawn. For spherical granules the shape and height of the curves is reproducible and if the granules show breakage, then the shape of the curve is closely related to crack formation and growth. A clear distinction can be made between the behavior of, for example, a prill granule, a high shear granule, fluid bed granules and glass beads. Larger granules due to addition of multiple layers show in general a larger elastic and plastic deformation upon breakage than smaller granules. The addition of coating layers around a yielding enzyme/ammonium sulphate layer also leads to good granule strength. Stiff elastic (crystalline) core materials resulted in extensive deformation of outer coatings and thus made the outer layers more vulnerable. Concentric multi-layer granules show better strength but also increased yielding. Good resistance to repeated-compression was found for elastic cores and yielding cores protected by thick layers of enzyme, and for particles coated with thick layers of coating. Good resistance was also found for yielding core materials that were protected by an extra plastic layer, indicating that plastic deformation of outside layers avoids yielding and thus improves granule strength. For elastic particles, failure appeared by yielding of the coatings around the core.

Elastic and plastic behavior of the granules can be identified by analysis of repeated compression curves. Coating glass beads or other perfect spheres with different polymer materials allows fundamental insight into the mechanical properties of the coating material. The repeated compression curves show that granule plasticity can be quantified. The repeated compression test gives much information about plasticity of granules. In particular, the difference between plastic compaction and plastic yielding can be recognized.

Other embodiments and advantages of the present invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A testing apparatus for determining the compression strength of a granule, said apparatus comprising:
   a bottom plate having a top surface;
   a platform having a top surface and an opposite bottom surface, said bottom surface facing said bottom plate, said top surface including a biasing portion and a contact portion for contacting a granule to be tested;
   a bottom biasing member positioned between the bottom plate and the platform and in contact with both the top surface of said bottom plate and the bottom surface of said platform, said bottom biasing member biasing said platform away from said bottom plate;
   an indentor having an indentor bottom surface facing said platform and a contact surface extending below said indentor bottom surface in a direction toward said platform, said contact surface facing said platform and for contacting a granule to be tested that is positioned on said platform;
   a top biasing member positioned between the top surface of said platform and the indentor bottom surface and in contact with both the indentor bottom surface and the biasing portion of said platform top surface, said top biasing member biasing said indentor away from said platform; and
   a measuring device to measure force exerted on a granule to be tested under force exertion conditions.

2. The testing apparatus of claim 1, wherein said indentor comprises: a top plate that includes said indentor bottom surface; and a contact member extending from said indentor toward said platform, said contact member having an upper end in contact with the top plate and a lower end comprising said contact surface.

3. The testing apparatus of claim 1, further comprising a force exertion device for exerting a force on said indentor to move said indentor in a direction toward said platform.

4. The testing apparatus of claim 1, wherein said bottom biasing member and said top biasing member have substantially the same force constants.

5. The testing apparatus of claim 1, wherein said bottom biasing member and said top biasing member are both springs.

6. The testing apparatus of claim 5, wherein said bottom biasing member and said top biasing member have substantially the same spring constants.

7. The testing apparatus of claim 5, wherein said bottom biasing member and said top biasing member are both Z-springs.

8. The testing apparatus of claim 1, wherein at least said top biasing member is provided with at least one strain gauge.

9. The testing apparatus of claim 8, wherein said one or more strain gauge measures the strain exerted parallel to a granule positioned between the contact surface of the indentor and the contact portion of the platform.

10. The testing apparatus of claim 9, further including a recording device to record the force exerted on a granule to be tested versus deformation of the granule.

11. The testing apparatus of claim 10, wherein said recording device is a plotting or graphing device.

12. The testing apparatus of claim 10, wherein said recording device includes an analog-to-digital interface and a computer.

13. The testing apparatus of claim 1, wherein the bottom biasing member and the top biasing member have respective force constants, and the force constants of the biasing members provide for a reduction in the compressive force exerted on a granule compressed between the contact portion of the platform and the contact surface of the indentor, upon breakage of the granule.

14. The testing apparatus of claim 3, wherein said apparatus has a mass spring system resonance frequency (f), said top biasing member has a force constant $C_1$, said bottom biasing member has a force constant $C_2$, said platform has an effective mass ($m_{eff}$), and the mass spring system resonance frequency (f) has a cycle time ($\tau=1/f$) according to the formula:

$$\tau=\sqrt{m_{eff}/(C1+C2)}.$$

15. The testing apparatus of claim 14, wherein said top biasing member and said bottom biasing member each comprises a Z-spring having top and bottom horizontal legs that remain substantially parallel to each other during compression of the Z-springs.

16. A testing apparatus for determining the compression strength of a granule, said apparatus comprising:

a bottom plate having a top surface;

a platform having a top surface and an opposite bottom surface, said bottom surface facing said bottom plate, said top surface including a biasing portion and a contact portion for contacting a granule to be tested;

a bottom biasing means for biasing said platform away from said bottom plate;

an indentor having an indentor bottom surface facing said platform and a contact surface extending below said indentor bottom surface in a direction toward said platform, said contact surface facing said platform and for contacting a granule to be tested that is positioned on said platform;

a top biasing means for biasing said indentor away from said platform; and a measuring means for measuring a force exerted on a granule to be tested under force exertion conditions.

17. The testing apparatus of claim 16 wherein said indentor comprises: a top plate that includes said indentor bottom surface; and a contact member extending from said indentor toward said platform, said contact member having an upper end in contact with the top plate and a lower end comprising said contact surface.

18. The testing apparatus of claim 16, further comprising a means for exerting a force on said indentor to move said indentor in a direction toward said platform.

19. The testing apparatus of claim 16, wherein said bottom biasing means and said top biasing means have substantially the same force constants.

20. The testing apparatus of claim 16, wherein at least said top biasing means is provided with a means for measuring strain.

21. The testing apparatus of claim 20, wherein said means for measuring strain measures the strain exerted parallel to a granule positioned between the contact surface of the indentor and the contact portion of the platform.

22. The testing apparatus of claim 21, further including a means to record data representative of force exerted on a granule to be tested versus deformation of the granule.

23. The testing apparatus of claim 16, wherein the bottom biasing means and the top biasing means have respective force constants, and the force constants of the biasing means provide for a reduction in the compressive force exerted on a granule compressed between the contact portion of the platform and the contact surface of the indentor, upon breakage of the granule.

24. The testing apparatus of claim 16, wherein said apparatus has a mass spring system resonance frequency (f), said top biasing means has a force constant $C_1$, said bottom biasing means has a force constant $C_2$, said platform has an effective mass ($m_{eff}$), and the mass spring system resonance frequency has a cycle time ($\tau=1/f$) according to the formula:

$$\tau=\sqrt{m_{eff}/(C_1+C_2)}.$$

25. A method of testing the compression strength of a granule, comprising:

providing a compression testing apparatus, said apparatus comprising a bottom plate having a top surface, a platform having a top surface and an opposite bottom surface, said bottom surface facing said bottom plate, said top surface including a biasing portion and a contact portion for contacting a granule to be tested, a bottom biasing member positioned between the bottom plate and the platform and in contact with both the top surface of said bottom plate and the bottom surface of said platform, said bottom biasing member biasing said platform away from said bottom plate, an indentor having an indentor bottom surface facing said platform and a contact surface extending below said indentor bottom surface in a direction toward said platform, said contact surface facing said platform and for contacting a granule to be tested that is positioned on said platform, a top biasing member positioned between the top surface of said platform and the indentor bottom surface and in contact with both the indentor bottom surface and said platform top surface, said top biasing member biasing said indentor away from said platform, and a measuring device to measure force exerted on a granule to be tested under force exertion conditions;

positioning a granule to be tested on said platform in contact with the contact portion of said platform and between the contact portion of the platform and the contact surface of the indentor;

exerting a force on said indentor in a direction toward said platform sufficient to move the contact surface of said indentor into contact with said granule and to exert a compressive force on said granule; and measuring the compressive force exerted on said granule.

26. The method of claim 25, further comprising continuing to exert said compressive force on said granule at least until said granule breaks.

27. The method of claim 25, further comprising recording the compressive force exerted on the granule versus the deformation of said granule during compression.

28. The method of claim 25, further comprising measuring the compressive force parallel to said granule, and measuring the force exerted on the granule by determining the difference between the recorded force exerted on said indentor and the recorded force parallel to said granule.

29. The method of claim 25, wherein said top and bottom biasing members are each Z-shaped springs that include a strain gauge.

30. The method of claim 25, wherein said top biasing member and said bottom biasing member each comprises a Z-spring having top and bottom horizontal legs that remain substantially parallel to each other during compression of the Z-springs.

31. The method of claim 27, further comprising analyzing the relationship between the recorded force exerted on the granule and the recorded deformation of the granule during compression and determining a breakage mechanism based on the analysis.

32. The method of claim 31, wherein said analyzing comprises comparing the recorded results with recorded results obtained from substantially identical testing on granules with known breakage mechanisms.

33. The method of claim 25, further comprising reducing the force exerted on the granule and repeating the exertion of force on the granule.

34. The method of claim 33, further comprising recording the compressive force exerted on the granule versus the deformation of said granule during the repeated exertion and reduction of force on the granule.

35. The method of claim 34, further comprising analyzing the deformation of the granule based on the recorded results.

36. The method of claim 35, wherein said analyzing comprises comparing the recorded results with recorded results obtained from substantially identical testing on granules with known repeated compression test characteristics.

* * * * *